(12) United States Patent
Roux et al.

(10) Patent No.: US 12,036,237 B2
(45) Date of Patent: *Jul. 16, 2024

(54) BROMIDE SOURCE FOR USE IN TREATING AUTISM SPECTRAL DISORDER

(71) Applicants: INSERM (INSTITUT NATIONAL DE LA SANTE ET DE LA RECHERCHE MEDICALE), Paris (FR); INRA, INSTITUT NATIONAL DE LA RECHERCHE AGRONOMIQUE, Paris (FR); CNRS, CENTRE NATIONAL DE LA RECHERCHE SCIENTIFIQUE, Paris (FR); UNIVERSITE DE STRASBOURG, Strasbourg (FR)

(72) Inventors: Sébastien Roux, Ribeauvillé (FR); Thierry Plouvier, Tours (FR); Julie Le Merrer, Monthodon (FR); Jérôme Becker, Semblançay (FR)

(73) Assignees: INSERM (INSTITUT NATIONAL DE LA SANTE ET DE LA RECHERCHE MEDICALE), Paris (FR); INSTITUT NATIONAL DE RECHERCHE POUR L'AGRICULTURE, L'ALIMENTATION ET L'ENVIRONNEMENT, Paris (FR); CNRS, CENTRE NATIONAL DE LA RECHERCHE SCIENTIFIQUE, Paris (FR); UNIVERSITE DE STRASBOURG, Strasbourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,694

(22) Filed: Apr. 20, 2023

(65) Prior Publication Data
US 2023/0256009 A1 Aug. 17, 2023

Related U.S. Application Data

(62) Division of application No. 16/464,403, filed as application No. PCT/EP2017/080726 on Nov. 28, 2017, now Pat. No. 11,666,599.

(30) Foreign Application Priority Data

Nov. 28, 2016 (GB) .................................. 1620095

(51) Int. Cl.
*A61K 33/00* (2006.01)
*A61K 31/522* (2006.01)
*A61P 25/00* (2006.01)

(52) U.S. Cl.
CPC ............ *A61K 33/00* (2013.01); *A61K 31/522* (2013.01); *A61P 25/00* (2018.01)

(58) Field of Classification Search
CPC ...................................................... A61P 25/00
See application file for complete search history.

(56) References Cited

U.S. PATENT DOCUMENTS

2018/0028499 A1* 2/2018 Baraban ............. A61K 31/4184

FOREIGN PATENT DOCUMENTS

WO    WO2012149472 A2 * 11/2012 ............. A61K 48/00

OTHER PUBLICATIONS

Bachmann et al, Psychopharmacological treatment in children and adolescents with autism spectrum disorders in Germany, Research in Developmental Disabilities 34 (2013) 2551-2563 (Year: 2013).*

* cited by examiner

*Primary Examiner* — Mark V Stevens
*Assistant Examiner* — Alparslan Asan
(74) *Attorney, Agent, or Firm* — WCF IP

(57) ABSTRACT

The present invention relates to a novel pharmaceutical use of bromide, i.e. the treatment of autism spectral disorder (ASD).

15 Claims, 22 Drawing Sheets

Time line of the experiments

Chronic bromide treatment fully restores social preference in *Oprm1* knockout mice Chronic bromide treatment restores social interaction and preference in *Fmr1* null mice Chronic bromide treatment normalizes social interaction and preference in *Shank3B* knockout mice Time line of behavioural experiments Effects of chronic bromide treatment on the main behavioural parameters assessed in the direct social interaction test Effects of chronic bromide treatment on the latency to feed in the novelty-suppressed feeding test Effects of chronic bromide treatment on locomotor activity measured by videotracking

BROMIDE SOURCE FOR USE IN TREATING AUTISM SPECTRAL DISORDER

The present invention relates to the use of bromides in the treatment of autistic spectrum disorder (ASD).

Bromides have a long history in the treatment of epilepsy and related convulsions. Thus, while being considered the ideal anti-epileptic drug for many years, the use of bromides has been somewhat superseded by the development of pentobarbitals and benzodiazepines. The activity and history of the anti-epileptic use of bromides is well summarised in the article by Suzuki S et al. (Epilepsy Res 1994 19 89-97) who describes the ability of bromide to potentiate GABAergic induced hyperpolarization and Friedlander W J (Arch Neurol 2000 57 1782-1785) who describes the rise and fall of bromide therapy in epilepsy. Further examples include Pearce J M S, "Bromide, the first effective antiepileptic agent" *J Neurol Neurosurg Psychiatry* 2002 72: 412 and Shorvon S D, Drug "Treatment of epilepsy in the century of the ILAE", *Epilepsia,* 50(Suppl. 3):69-130, 2009.

Despite the demise in the use of bromides as anti-epileptic, there have still been reports of its use in this therapeutic scenario. For example, Caraballo R et al, "Epilepsy of infancy with migrating focal seizures: Six patients treated with Bromide" *Seizure* 23 (2014): 899-902 and Higurashi N et al, "PCDH19-related female-limited epilepsy: further details regarding early clinical features and therapeutic efficacy" *Epilepsy Research* (2013) 106, 191-199.

In Dravet Syndrome, bromides appear to be widely used, together with Stiripentol as in: Arzimanoglou A: "Dravet syndrome: From electroclinical characteristics to molecular biology", *Epilepsia,* 50(Suppl. 8):3-9, 2009, and Chiron C: "Current therapeutic procedures in Dravet syndrome" *Developmental Medicine & Child Neurology* 2011, 53 (Suppl. 2): 16-18.

Bromides are commonly used in the treatment of veterinary epilepsy, especially in dogs as described in Boothe D M et al "Comparison of phenobarbital with bromide as a first-choice antiepileptic drug for treatment of epilepsy in dogs" *Journal of the American Veterinary Medical Association* May 1, 2012, Vol. 240, No. 9, Pages 1073-1083.

Autism is lifelong neurological condition characterised by difficulty in communicating and forming relationships. Such social aspects of the disorder are frequently accompanied by physical and behavioural aspects. Due to the variety of presentations of autism, the term currently preferred is "autistic spectrum disorder" (ASD) which better reflects the range of symptoms observed within this disorder.

Defined diagnostic criteria for ASD or autistic disorder have been described for example by WHO e.g. Section F84 of ICD-10 (World Health Organisation 1992) available at http://www.who.int/classifications/icd/en/GRNBOOK.pdf, the API-R and Autism Diagnostic Observation Schedule (Generic) (ADOG) available at for example, http://www.hogrefe.co.uk/autism-diagnostic-observation-schedule-ados.html or DSM V available at http://www.dsm5.org/. The diagnostic criteria as they appear in DSM-V (May 2013) are available at https://www.autismspeaks.org/what-autism/diagnosis/dsm-5-diagnostic-criteria. For the purposes of the present invention, reliance is preferably placed in the DSM-V definitions and characterisations of ASD.

There is no cure for autism or ASD and drug therapy is most usually directed to particular symptoms of behaviours such as anxiety, attention difficulties, depression, obsessive-compulsive disorder, sleep difficulties and severe maladaptive behavioural problems. For example, the U.S. Food and Drug Administration (FDA) has approved risperidone and aripiprazole for the treatment of irritability associated with autistic disorder in children and adolescents aged 5 to 17 years, including symptoms of aggression toward others, deliberate self-injuriousness, temper tantrums, and quickly changing moods.

A number of medications are prescribed for treatment of specific ASD-related symptoms, such as stimulants, serotonin reuptake inhibitors, atypical antipsychotics, $\alpha$-2 agonists, anticonvulsants, omega 3 fatty acids and melatonin. Families also often use various complementary and alternative medical treatments. Many of these treatments are unsupported by scientific studies. Alternative treatments include nutritional supplements (Vitamin B6, magnesium ion, dimethyl glycine, and cod-liver oil), anti-infectives (antibiotics, antifungals, and antivirals), immunoglobulins, secretin, chelation medications, gastrointestinal medication, elimination or special diets (gluten or casein free), and hyperbaric oxygen administration.

Selective serotonin re-uptake inhibitors (SSRIs) like fluoxetine, fluvoxamine, citalopram and/or sertraline are approved by the FDA for children at different ages with obsessive-compulsive disorder. However, the use of SSRI's in Autism is expected to reduce the frequency and intensity of repetitive behaviours; decrease anxiety, irritability, tantrums, and aggressive behaviour; and improve eye contact. Another older tricyclic antidepressant, clomipramine is also used.

Antipsychotics like haloperidol, olanzapine and ziprasidone may be given in an effort to address aggressive behaviour whereas risperidone may be given to treat symptomatic irritability. But these medicines can have side effects, including sleepiness, tremors, and weight gain.

Clonidine and guanfacine are used for impulsive and aggressive behaviours, whereas lithium, carbamazepine and valproic acid are prescribed to stabilize children who are occasionally aggressive.

Stimulant medications like Methylphenidate are prescribed to decrease impulsivity and hyperactivity in higher functioning children.

The variety of pharmacological agents used to treat different aspects of ASD demonstrate the wide range of pharmacological neurotransmitters and mediators implicated in this range of disorders.

Among the many agents suggested for use in an effort to alleviate one or more autistic symptoms is the diuretic bumetanide. Lemonnier et al (*Transl Psychiatry* 2012 2 e202; doi:10.1038/tp.2012.124) describe the administration of bumetanide to a cohort of autistic children aged 3-11. The rationale for using bumetanide lies in the observed alterations in GABAergic signals in autism. On the basis that some autistic symptoms arise from GABAergic excitation and resultant increase in intracellular chloride, inhibition of the chloride importer NKCC1 by bumetanide was considered a viable strategy. The authors report a favourable result in respect of certain parameters. Despite the inability of bumetanide to cross the blood brain barrier, this compound is described as having a central effect.

Given the continued need to identify an effective treatment for autism, the present invention seeks to provide a new approach to the treatment of autism/ASD.

SUMMARY OF THE INVENTION AND PREFERRED EMBODIMENTS

The present invention is based on the unexpected finding that one or more clinical symptoms of autism spectral disorder (ASD) may be improved and or relieved by the administration of a source of bromide to an autistic patient. The surprising activity of bromide in patients suffering from ASD offers the opportunity to provide an alternative to the currently accepted therapies each of which have deficiencies. In particular, it would be desirable to treat autism in a manner that is not dependent on the presence of specific receptor, with an active agent that has a wide therapeutic window and an onset of action commensurate with both chronic and transient treatment of ASD symptoms. It would be particularly desirable to provide a treatment that was effective in the social deficit aspect of ASD.

Thus, in one embodiment the present invention provides a source of bromide for use in the treatment of ASD.

In particular, it has been observed that the source of bromide is capable of improving cognitive flexibility, relieving social deficit and/or exacerbated anxiety associated with ASD.

Any pharmaceutically acceptable source of bromide is suitable for use in the present invention. Preferably, the pharmaceutically acceptable source of bromide is selected from bromide salts such as potassium bromide, sodium bromide, ammonium bromide, calcium bromide, calcium bromolactobionate, calcium galactogluconate bromide, calcium bromide lactobionate hexahydrate, calcium bromogalactogluconate, calcium bromolactobionate, clidinium bromide, ferrous bromide, gold tribromide, hydrogen bromide, iron bromide, lithium bromide, magnesium bromide, radium bromide, strontium bromide, alone or in combination, acecarbromal, bromazepam, bromazine, bromisoval, bromoforme, bromperidol, carbromal magnesium aspartate hydrobromide, galantamine bromohydrate and theobromine.

Bromide salts dissociate already in the stomach, in such a way that the counter-ion role is limited for therapeutic efficacy. Solid, effervescent and liquid formulations of a single bromide salt are present in the third edition of the US National Formulary (1906). Bromides have also traditionally been given in a solution consisting of sodium, potassium and ammonium salts of bromide in equal amounts (by weight) of each. The "Elixir of Three Bromides" contains 240 mg/mL of bromide salt. An "Elixir of Five Bromides" has also been marketed, by adding calcium and lithium bromide salts. More recently, solid (tablet or capsule) formulations of potassium or sodium bromide have been developed. Injectable and/or rectal formulations of bromide may also be considered, as well as more recent modes of administration like percutaneous, intra-nasal and sublingual administration.

Further suitable sources of bromide include aclidinium bromide, anisotropine methylbromide, arsenic tribromide, azoximer bromide, benzalkonium bromide, benzododecinium bromide, bupropion hydrobromide, butropium bromide, carbaethopendecine bromide, cethexonium bromide, cetrimonium bromide, cetyltrimethylammonium bromide, ciclonium bromide, cimetropium bromide, citalopram hydrobromide, clidinium bromide, darifenacin hydrobromide, demecarium bromide, decamethonium bromide, dextromethorphan hydrobromide, distigmine bromide, dodeclonium bromide, dodecyltrimethylammonium bromide, domiphen bromide, doxacurium bromide, edrophonium bromide, eletriptan hydrobromide, ethidium bromide, fazadinium bromide, galantamine hydrobromide, glycopyrrolate bromide, glycopyrronium bromide, hexadecyltrimethylammonium bromide, hexafluorenium bromide, homatropine methylbromide, homidium bromide, hydroxyamphetamine hydrobromide, hyoscine bromide, hyoscine butyl bromide, hyoscine N butyl bromide, ipratropium bromide, lithium bromide, mepenzolate bromide, methacholine bromide, methantheline bromide, methanthelinium bromide, methscopolamine bromide, methylnaltrexone bromide, methylscopolamine bromide, mivacurium, neostigmine bromide, octylonium bromide, otilonium bromide, oxitropium bromide, oxyphenonium bromide, pancuronium bromide, perfluorooctyl bromide, pinaverium bromide, pipecuronium bromide, pipenzolate bromide, prifinium bromide, propantheline bromide, prostigmin bromide, pyridostigmine bromide, radium bromide, rapacuronium bromide, rocuronium bromide, scopolamine hydrobromide, scopolamine butylbromide, tarloxotinib bromide, tetradecyltrimethylammonium bromide, thonzonium bromide, timepidium bromide, tiotropium bromide, tiquizium bromide, umeclidinium bromide, valethamate bromide, vecuronium bromide, vortioxetine hydrobromide, xylyl bromide, yttrium bromide, zinc bromide.

In a preferred embodiment the source of bromide is a bromide salt selected from potassium, sodium, ammonium, calcium or lithium salts, alone or mixtures of 2, 3, 4 or 5 of said salts, for example a mixture of sodium, potassium and ammonium salts (Elixir of Three Bromides) or a mixture of sodium, potassium, calcium, lithium and ammonium salts (Elixir of Five Bromides). Most preferably, the source of bromide includes sodium or potassium bromide alone or in combination with one or more other sources of bromide, most preferably potassium bromide is used alone or in combination with one or more other sources of bromide.

In accordance with the present invention, the source of bromide may be administered alone or in combination with one or more pharmaceutically active compounds having a role in treating ASD, hereinafter referred to as the "second active pharmaceutical agent".

Suitable second pharmaceutical agents to be used in combination with a source of bromide include compounds known to have an effect on a symptom associated with ASD such as stimulants, serotonin reuptake inhibitors such as fluoxetine, fluvoxamine, citalopram and/or sertraline, antipsychotics such as aripiprazole, haloperidol, olanzapine, ziprasidone or risperidone, α-2 agonists, anticonvulsants, omega 3 fatty acids, melatonin, methylphenidate and bumetanide. Preferably, the second agent is selected from risperidone, aripiprazole, olanzapine, oxytocin or bumetanide, more preferably from oxytocin or bumetanide.

In a preferred embodiment, the source of bromide is administered in combination with a second agent selected to counter bromide-induced sleepiness. Such second agents include caffeine[1] as described in *The Standard Formulary, 10th Edition* (1900) by Albert Ethelbert Ebert and A. Emil Hiss, (G. P. Engelhard, Chicago), where the Elixir of Three Bromides includes caffeine as an active ingredient. Crotzer's Effervescent Bromo-Mint with Caffeine One Dose Bottle was another bromide-caffeine combination.

[1] H. Druckrey, E. Müller, M. Stuhlmann, Die Beeinflussung der sedativen Wirkung durch Antipyretika und Coffein *Naunyn-Schmiedebergs Archiv für experimentelle Pathologic and Pharmakologie* 185 (2-3) 1937, 221-226; *Physiol. Abst.* 22 (1937), 1101 and *Pharmaceutical Abstracts*, Vol IV, n°9, p434 (1938)

As used herein, the terms "combination" and "in combination with" refer to both separate and sequential administration of the source of bromide and the second active pharmaceutical agent.

When the agents are administered sequentially, either the source of bromide or the second agent may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

The diagnosis and identification of ASD is set out in the guidelines referred to above (Section F84 of ICD-10, ADOG or DSM-V). Any patient having received such a diagnosis of ASD is suitable for treatment in accordance with the present invention. The administration of a source of bromide to such a patient may give rise to improvement in one or more symptoms of ASD. Such symptoms include reduced social interaction, absence of interest in others, preference to remain alone, repetitive behaviours, unusual interests or behaviours, absence of understanding of personal space boundaries, avoidance or resistance to physical contact, repetitive motions, routine behaviours, impulsivity, delays in social and learning skills.

In particular, bromide will provide improvement in cognitive flexibility, relieving social deficit and or exacerbated anxiety associated with autism.

Improvement in said symptoms may be measured in the manner set out in the guidelines referred to. For example, with respect to cognitive flexibility, relieving social deficit and or exacerbated anxiety associated with ASD, an improvement may be observed by a reduction in the severity of social communication impairments and a reduction in the severity of restricted, repetitive patterns of behaviour. In case of comorbid anxiety disorder, an improvement of anxiety symptoms is also expected.

The present invention also has applicability in a veterinary environment. Many pets, especially dogs suffer with psychological and behavioural problems that require therapeutic intervention. For example, tail-chasing by dogs may have a psychological basis that would benefit from therapeutic intervention by the administration of a source of bromide as described above.

A further embodiment of the present invention therefore relates to a source of bromide for use in the treatment of psychological and behavioural problems in pets. Preferably, the pet is a dog.

The source of bromide suitable for use in this further embodiment is identical to the sources described above.

MODES OF ADMINISTRATION OF BROMIDE

Figure 1:
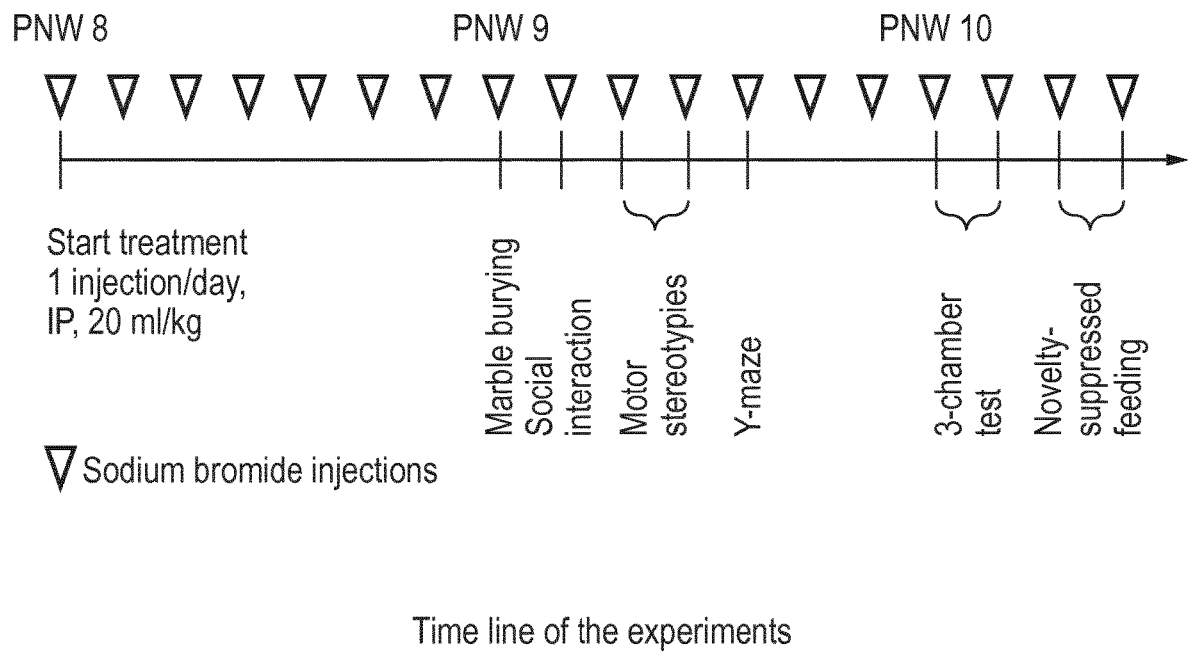
FIG. 1 shows the duration of chronic treatment and order of behavioural assays of Example 1.

The suitable sources of bromide for use according to the invention may be administered as the raw material but the active ingredients are preferably provided in the form of pharmaceutical compositions.

Formulations of the invention include those suitable for oral, parenteral (including subcutaneous e.g. by injection or by depot tablet, intravenous, intramuscular, subcutaneous, intrathecal-intraventricular, epidural, intradermal. intradermal, transdermal, intrathecal, intramuscular e.g. by depot and intravenous), rectal, vaginal and topical (including dermal, percutaneous, patches, intranasal, buccal and sublingual), ocular (drops or palpebral) or in a form suitable for administration by inhalation, infusors or insufflation administration. The most suitable route of administration may depend upon the condition and disorder of the patient.

Preferably, the compositions of the invention are formulated for oral or topical administration. In a preferred embodiment, the composition is an oral solution, suspension, syrup or linctus. Alternatively, if a solid dosage form is preferred, this preferably takes the form of tablets, capsules or a powder or granules.

The formulations may conveniently be presented in unit dosage form and may be prepared by any of the methods well known in the art of pharmacy e.g. as described in *"Remington: The Science and Practice of Pharmacy"*, Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Compositions for use according to the invention may be presented in a pack or dispenser device which may contain one or more unit dosage forms containing the active ingredients. The pack may, e.g. comprise metal or plastic foil, such as a blister pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The compounds for use in the present invention are commercially available and/or may be prepared using conventional methods known in the art.

The administration of the combination of the invention by means of a single patient pack, or patients packs of each composition, including a package insert directing the patient to the correct use of the invention is a desirable feature of this invention.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day.

The amount of bromide to be administered to bring about the desired effect must be calculated on the basis of the bromide ion content of the source of bromide e.g. if sodium bromide is being used, the bromide content of the product must be determined. Preferably, the amount of bromide to be administered will typically be from 3.0 mg/kg to 100 mg/kg, preferably from 6.0 mg/kg to 50 mg/kg.

When calculating an appropriate dosage of bromide, the physician may take into account the patients diet and other drug/supplement therapy. For example, the following factors may influence the level of bromide therapy required to attain the desired effect;

Hydration—Diet of the patient: for the dose claimed to be appropriate, proper food intake and hydration of the patient must be taken care of and controlled, Ketogenic Diet: co-treated with ketogenic diet will impact on the dose of bromide required, Sodium Chloride status of the patient: the patient should receive a normal daily intake of sodium chloride and/or not be on a treatment that may have an impact on the sodium chloride balance, like diuretics. Otherwise, bromide dosage should be adapted accordingly, Other medicines, dietary supplements, which could introduce additional bromide to the patient, when bromide is a counterion to the supposed active ingredient, Other halogens that may increase the total halogen concentration in body fluids, for instance iodine, fluorine or certain dietary salts.

The desired dose may conveniently be presented in a single dose or as divided doses administered at appropriate intervals, e.g. as two, three, four or more sub-doses per day.

The effect of bromide in various animal models of ASD is demonstrated in the following non-limiting examples. The source of bromide can be varied without any expectation of any change in effect.

Example 1

Example 1 completes and extends Example 2. Additional cohorts of mice lacking the Oprm1 gene were tested and pooled with previous ones to allow assessing gender influence on the effects of chronic bromide treatment. An additional dose of 125 mg/kg of bromide was evaluated in such large cohorts. The effects of bromide in the Oprm1 model were compared to these of bumetanide administered following the same protocol at the dose of 0.5 mg/kg. Finally, the dose of 250 mg/kg was chosen to assess the effects of bromide treatment in two additional genetic mouse models of autism spectrum disorders (ASD), mice lacking the Fmr1 gene (modelling Fragile X syndrome) and mice lacking the SHANK3B protein isoform.

Material and Methods

Subjects

Mice Lacking the Mu Opioid Receptor (Oprm1$^{-/-}$)

Mice lacking the mu opioid receptor recapitulate a remarkable number of autistic-like behavioural features (Crawley, 2007): marked social interaction deficits, reduced maternal attachment, altered communication skills (Cinque et al, 2012; Moles et al, 2004; Wohr et al, 2011) and stereotyped and perseverative behaviours (Becker et al, 2014) as regards core symptoms (DSM-5); aggressiveness, exacerbated anxiety, motor clumsiness, increased susceptibility to seizures (Becker et al, 2014), impaired spatial learning (Jamot et al, 2003), lowered nociceptive thresholds (Gaveriaux-Ruff and Kieffer, 2002) and reduced gastrointestinal motility (Roy et al, 1998) as regards comorbid symptoms. Based on such unique facial validity, Oprm1$^{-/-}$ were proposed as a unique monogenic mouse model of autism (Becker et al, 2014; Oddi et al, 2013). Moreover, Oprm1$^{-/-}$ mice also display anatomical, neurochemical and genetic landmarks of autism, such as altered inhibitory/excitatory neurotransmission balance, altered morphology of striatal synapses and modified expression of several marker genes of autism (Becker et al, 2014). Importantly, genetic studies have detected discrete invalidating mutations of the Oprm1 gene in some ASD patients (SFARIgene$^{2.0}$ database), suggesting that such invalidation may contribute to the development of an autistic syndrome, and providing construct validity for the Oprm1$^{-/-}$ mouse model. Finally, mu opioid receptor null mice display less motor stereotypies under risperidone treatment (Becker et al, 2014), show improved social skills after early behavioral intervention (Garbugino et al, 2016) and oxytocin administration (Gigliucci et al, 2014) as demonstrated for patients, proving predictive validity for translational research.

The Oprm1$^{-/-}$ mouse line (B6.129S2-Oprm1$^{tm1Kff/J}$) was acquired from Jackson Laboratories (Farmington, USA). Male and female mutant and wild-type mice aged 8-10 weeks were bred in-house on an identical hybrid background: 50% 129SVPas-50% C57BL/6J. Oprm1$^{+/+}$ and Oprm1$^{-/-}$ pups were nurtured by Oprm1$^{+/+}$ and Oprm1$^{-/-}$ parents, respectively. Animals were group housed (2-5 animals per cage) and maintained on a 12 hr light/dark cycle (lights on at 7:00 AM) at controlled temperature (21±1° C.). Food and water were available ad libitum throughout all experiments, unless otherwise stated.

Mice Lacking the Fmr1 Gene (Fmr1$^{-/-}$)

Fragile X Syndrome (FXS) is the most common known single gene cause of autism spectrum disorder (ASD) (Abbeduto et al, 2014; Budimirovic and Kaufmann, 2011). A genetic mouse model of FXS was engineered in 1994 by inducing a knock-out mutation in the mouse Fmr1 gene, which has 98% homology with its human orthologue, FMR1 (1994). These Fmr1$^{-/-}$ animals have been widely used since then to investigate the function of FMRP and to design novel therapeutic strategies to relieve medical issues and behavioral deficits in patients with FXS (Bardoni et al, 2006; Lozano et al, 2014; Maurin et al, 2014). Fmr1$^{-/-}$ mice display altered social communication (Rotschafer et al, 2012; Roy et al, 2012), aggressiveness (Pietropaolo et al, 2011), deficient social interaction/preference and social anxiety (McNaughton et al, 2008; Spencer et al, 2011; Spencer et al, 2005). Moreover, they show reduced behavioral flexibility in several cognitive reversal-learning tasks (Consortium, 1994; D'Hooge et al, 1997; Van Dam et al, 2000; Yan et al, 2004) and stereotyped behavioral responses in various tests (Pietropaolo et al, 2011; Spencer et al, 2011). Therefore, Fmr1 null mice recapitulate all core symptoms of autism, as well as most frequent comorbid symptoms of ASD and FXS (Argyropoulos et al, 2013; Crawley, 2007; Kidd et al, 2014; Silverman et al, 2010): increased (defensive/conflict) anxiety, intellectual disability, hyperactivity, higher susceptibility to seizures and motor clumsiness (Padmashri et al, 2013; Roy et al, 2011). As such, Fmr1$^{-/-}$ mice are considered as an excellent preclinical model for studying autistic traits (Oddi et al, 2013; Spencer et al, 2011).

The Fmr1 mutant line was acquired from Rob Willemsen (Erasmus MC, Rotterdam, Netherlands). Male and female mutant and wild-type mice aged 8-10 weeks were bred in-house on a C57BL/6J background. Animals were group housed (2-5 animals per cage) and maintained on a 12 hr light/dark cycle (lights on at 7:00 AM) at controlled temperature (21±1° C.). Food and water were available ad libitum throughout all experiments, unless otherwise stated.

Mice Bearing Mutations in the Shank3 Gene (Shank3B$^{-/-}$)

In humans, heterozygous mutations in the SHANK3 gene, coding for the synaptic scaffolding protein SHANK3 (Monteiro and Feng, 2017), have been associated with ASD and Phelan-McDermid syndrome (Durand et al, 2007; Harony-Nicolas et al, 2015). To investigate the pathophysiological consequences of SHANK3 haploinsufficiency, several rodent models targeting different isoforms of the SHANK3 protein have been generated. Despite some discrepancies, they consistently show behaviors indicative of ASD, with little impact of genetic background (Harony-Nicolas et al, 2015; Varghese et al, 2017). Notably, mice bearing a partial deletion of the Shank3 gene leading to the loss of the SHANK3B isoform (Shank3B$^{-/-}$ display severe deficits in social behavior, including perturbed social interactions and impaired recognition of social novelty, as well as excessive and repetitive grooming and anxiety-like behaviour (Peca et al, 2011). These animals are considered by the scientific community as a well-validated model of non-syndromic autism.

The Shank3B mutant line (B6.129-Shank3$^{tm2Gfng/J}$) was acquired from Jackson Laboratories (Farmington, USA). Male and female mutant and wild-type mice aged 8-10 weeks were bred in-house on a C57BL/6J background. Animals were group housed (2-5 animals per cage) and maintained on a 12 hr light/dark cycle (lights on at 7:00 AM at controlled temperature (21±1° C.). Food and water were available ad libitum throughout all experiments, unless otherwise stated.

Drug Treatment

Sodium bromide (anhydrous, Sigma-Aldrich, Saint-Quentin, France) dissolved in saline solution (NaCl, 0.9%) at the dose of 250 or 500 mg/kg, or vehicle (NaCl, 0.9%), was administered intraperitoneally once a day for 19 days in a volume of 20 ml/kg. On testing days, bromide was administered 30 min before behavioural assays. Bumetanide (Tocris, provided by Bio-Techne, Lille, France) dissolved in NaCl 0.9% at the dose of 0.5 mg/kg (Deidda et al, 2015) or vehicle was administered intraperitoneally once a day for 19 days in a volume of 20 ml/kg.

Behavioural Testing

Behavioural assays started after a week of daily bromide (or bumetanide) treatment. These assays were performed successively in each cohort of animals and the order of the tests was arranged to minimize the effect of stress on further evaluation (time line in FIG. 1). Social abilities were explored using the direct social interaction and the three-chamber tests; stereotyped behavior was assessed by scoring motor stereotypies and measuring spontaneous alternation in a Y-maze (perseveration behavior). Anxiety-like behavior was evaluated in the marble burying and novelty-suppressed feeding tests (Becker et al, 2014; Tabet et al, 2016). Direct social interaction and novelty suppressed feeding were performed in 4 equal square arenas (50×50 cm) separated by 35 cm-high opaque grey Plexiglas walls over black Perspex® floors (View Point, Lyon, France).

Direct social interaction. A pair of experimental, non-cage mate, gender, genotype and treatment-matched mice was introduced in each arena for 10 min (15 lx). The number and duration of nose (sniffing nose-to-nose) and paw contacts, as well as the number of following, grooming, rearing and circling episodes were scored on video recordings. A total time in social contact was calculated by adding time in nose contact and time in paw contact. Grooming episodes that occurred within 5 sec after a nose or paw contact where scored as "grooming immediately after a close contact".

Three-chamber social novelty preference test. The test apparatus consisted of a black rectangular plastic box; partitions (transparent walls) divided the box into three equal chambers (40×21×22 cm). Two sliding doors (8×6 cm) allowed transitions between chambers. Cylindrical wire cages (21×8.5 cm, 0.5 cm diameter-rods spaced 1 cm apart) were used to contain the stimulus mice. Stimulus mice (8-10-week-old gender- and genotype-matched grouped-housed wild-type mice, socially naive to the experimental animals) were habituated to confinement in wire cages for 2 days (20 min/day). For the sociability test (15 lx), the test animal was introduced to the middle chamber and the dividers were raised to allow the animal exploring the apparatus for a 10-min habituation (wire cages empty). Interaction phase started when an unfamiliar mouse (stimulus mouse) was introduced into a wire cage in one of the side-chambers; a soft toy mouse (8×10 cm) was introduced in the second wire cage as a control for novelty. The dividers were raised and the experimental animal was allowed to freely explore the apparatus (10 min). The time spent in each chamber, number of entries in each compartment and time spent in close (nose or paw) contact with the stimulus mouse versus wire cage containing the toy (except climbing) as well as the number of such contacts were scored on video recordings; the mean duration of close contacts was calculated from previous measures. The relative position of the stimulus mouse was counterbalanced between groups.

Motor stereotypies. Mice were individually placed in standard cages filled with 3-cm deep fresh sawdust for 10 min at 40 lx. Numbers of head shakes, rearing, burying, grooming and circling episodes as well as the total time spent burying were measured by direct observation. Mean duration of burying events was calculated from previous measures.

Y-maze exploration. Spontaneous alternation was assessed in a Y-maze consisting of three Plexiglas arms (18×15×15 cm) covered with distinct patterns (15 lx). Each mouse was placed at the centre of an arena and allowed to freely explore the maze for 5 min. The total number of arm entries, as well as the exact sequence of these entries, was quoted on video-recordings. Spontaneous alternations (SA), i.e. successive entries into each arm forming overlapping triplet sets, alternate arm returns (AAR) and same arm returns (SAR) were scored, and the percentage of SA, AAR and SAR was calculated as following: total/(total arm entries−2)*100.

Marble burying. Mice were introduced individually in transparent cages (21×11×17 cm) containing 20 glass marbles (diameter: 1.5 cm) evenly spaced on 4-cm deep fresh sawdust. To prevent escapes, each cage was covered with a filtering lid. Light intensity in the room was set at 30 lux. The animals were removed from the cages after 15 min, and the number of marbles buried more than half in sawdust was quoted.

Novelty-suppressed feeding. Novelty-suppressed feeding (NSF) was measured in 24-hr food-deprived mice, isolated in a standard housing cage for 30 min before individual testing. Three pellets of ordinary lab chow were placed on a white tissue in the centre of each arena, lit at 60 lx. Each mouse was placed in a corner of an arena and allowed to explore for a maximum of 15 min. Latency to feed was measured as the time necessary to bite a food pellet. Immediately after an eating event, the mouse was transferred back to the home cage (free from cage-mates) and allowed to feed on lab chow for 5 min. Food consumption in the home cage was measured.

Locomotor activity. Locomotor activity was assessed in clear cages (21×11×17 cm) placed over a white Plexiglas infrared-lit platform. Light intensity of the room was set at 15 lx. The trajectories of the mice were analyzed and recorded via an automated tracking system equipped with an infrared-sensitive camera (Videotrack; View Point, Lyon, France). To focus on forward activity, only movements which speed was over 6 cm/s were taken into account for the measure of locomotor activity. Behavioral testing started when the animals were placed in the activity boxes for a 30 min-habituation period. They were then injected with either vehicle or sodium bromide (250 or 500 mg/kg) and locomotor activity was monitored for further 90 min.

Time Line of Drug Treatment and Behavioural Testing

Schedule and duration of chronic treatment as well as order of behavioural assays are displayed in FIG. 1. Testing order was chosen to limit the impact of stress on further behavioral assessments.

Statistical Analyses

Statistical analyses were performed using Statistica 9.0 software (StatSoft, Maisons-Alfort, France). Statistical significance was assessed using two-, three-way or four-way analysis of variance (gender, genotype, dose and stimulus-repeated measure-effects) followed by Newman-Keules post-hoc test. For all comparisons, values of $p<0.05$ were considered as significant.

Results
Oprm1$^{-/-}$ Mice
Measures of Sociability

Deficient social interactions are the most remarkable core symptom of autism in humans. We assessed the effects of chronic bromide treatment on social abilities in Oprm1$^{-/-}$ mice and wild-type counterparts using two tests, the direct social interaction test and the three-chamber test.

In the direct social interaction test (cf. FIG. 2A), chronic bromide treatment (125, 250 and 500 mg/kg versus saline) demonstrated beneficial effects by dose-dependently increasing, in Oprm1$^{-/-}$ animals, the total time spent in social contact (genotype effect: $F_{1,127}$=16.5, p<0.0001; gender effect: $F_{1,127}$=13.9, p<0.0001; dose effect: $F_{3,127}$=30.9, p<0.0001; genotype×dose: $F_{3,127}$=25.6, p<0.0001; genotype×gender×dose: $F_{3,127}$=5.3, p<0.01), the number, time spent in and duration of nose and paw contacts (number of nose contacts: gender effect: $F_{1,127}$=8.1, p<0.01; dose effect: $F_{3,127}$=10.3, p<0.0001; genotype×dose: $F_{3,127}$=9.4, p<0.0001; genotype×gender×dose: $F_{3,127}$=3.5, p<0.05; time spent in nose contact: genotype effect: $F_{1,127}$=16.9, p<0.0001; gender effect: $F_{1,127}$=13.2, p<0.0001; dose effect: $F_{3,127}$=27.9, p<0.0001; genotype×dose: $F_{3,127}$=23.6, p<0.0001; genotype×gender×dose: $F_{3,127}$=5.1, p<0.001; nose contact duration: genotype effect: $F_{1,127}$=16.5, p<0.001; gender effect: $F_{1,127}$=13.9, p<0.0001; dose effect: $F_{3,127}$=30.9, p<0.0001; genotype×dose: $F_{3,127}$=25.6, p<0.0001; genotype×gender×dose: $F_{3127}$=5.3, p<0.01; number of paw contacts: genotype effect: $F_{1,127}$=8.9, p<0.001; dose effect: $F_{3,127}$=29.4, p<0.0001; genotype×dose: $F_{3,127}$=15.7, p<0.0001; time spent in paw contact: gender effect: $F_{1,127}$=4.9, p<0.01; dose effect: $F_{3,127}$=23.0, p<0.0001; genotype×dose: $F_{3,127}$=14.4, p<0.0001; paw contact duration: genotype effect: $F_{1,127}$=48.1, p<0.0001; dose effect: $F_{3,127}$=22.3, p<0.0001; genotype×dose: $F_{3,127}$=19.9, p<0.0001) and the number of following episodes (dose effect: $F_{3,127}$=9.3, p<0.0001; genotype×gender×dose: $F_{3,127}$=2.7, p<0.05).

Bromide administration also reduced the number of grooming episodes (genotype effect: $F_{1,127}$=5.2, p<0.05; dose effect: $F_{3,127}$=19.3, p<0.0001; genotype×dose: $F_{3,127}$=5.2, p<0.01) and, more specifically, the number of grooming episodes occurring immediately after a social contact (genotype effect: $F_{1,127}$=34.7, p<0.0001; dose effect: $F_{3,127}$=33.7, p<0.0001; genotype×dose: $F_{1,127}$=36.4, p<0.0001) in Oprm1$^{-/-}$ animals (FIG. 2A). Gender effects indicate that chronic bromide administration at the highest doses tested (250 and 500 mg/kg) was more efficient in increasing social interaction parameters (time spent in social contact, time spent in nose contact, nose contact duration and following) in male than in female Oprm1$^{-/-}$ mice in this test (FIG. 2B). Altogether, these results reveal that chronic bromide treatment can restore direct social interaction in mu opioid null mice.

Under the same conditions, chronic bumetanide (0.5 mg/kg versus saline) increased, but failed to completely rescue, the time spent in social contact (genotype effect: $F_{1,59}$=73.4, p<0.0001; genotype×dose: $F_{1,59}$=10.0, p<0.01), time spent in (genotype effect: $F_{1,59}$=68.9, p<0.0001; genotype×dose: $F_{1,59}$=9.2, p<0.001) and duration of nose contacts (genotype effect: $F_{1,59}$=342.9, p<0.0001; genotype × dose: $F_{1,59}$=9.4, p<0.01) in knockout mice compared to wild-type animals. This treatment had no significant effect on the number of nose contacts (genotype effect: $F_{1,59}$=7.8, p<0.01; dose effect: $F_{1,59}$=5.8, p<0.001; genotype×dose: $F_{1,59}$=5.2, p<0.05) and the number of (genotype effect: $F_{1,59}$=46.7, p<0.0001; dose effect: $F_{1,59}$=13.0, p<0.05; genotype×dose: $F_{1,59}$=9.6, p<0.01), time spent in (genotype effect: $F_{1,59}$=22.9, p<0.0001; dose effect: $F_{1,59}$=6.0, p<0.05; genotype×dose: $F_{1,59}$=5.2, p<0.05) and duration of paw contacts (genotype effect: $F_{1,59}$=76.4, p<0.0001; dose effect: $F_{1,59}$=4.9, p<0.05) in mutant mice.

Bumetanide, however, normalized the number of (genotype effect: $F_{1,59}$=5.3, p<0.05; dose effect: $F_{1,59}$=21.4, p<0.0001) and time spent in grooming episodes (dose effect: $F_{1,59}$=11.9, p<0.01) and, more specifically, the number of grooming episodes following a social contact (genotype effect: $F_{1,59}$=27.9, p<0.0001; dose effect: $F_{1,59}$=27.9, p<0.0001; genotype×dose: $F_{1,59}$=19.6, p<0.0001) in Oprm1$^{-/-}$ mice (FIG. 2B). These data indicate that, at this dose, bumetanide only partially restored social interaction in mice lacking the mu opioid receptor. Statistical power in bumetanide experiments was not sufficient to test gender effects.

In the three-chamber test (cf. FIG. 3), chronic bromide restored social preference in Oprm1$^{-/-}$ animals in a dose dependent manner as shown by restored difference (preference for the mouse over the toy) in time spent in compartments (stimulus effect—toy mouse versus living mouse—: $F_{1,121}$=106.6, p<0.0001; stimulus×genotype×dose: $F_{3,121}$=3.0, p<0.05; stimulus×gender×dose: $F_{3,121}$=2.7, p=0.5), number of nose contacts (gender effect: $F_{1,121}$=4.7, p<0.05; dose effect: $F_{3,121}$=3.7, p<0.05; stimulus effect: $F_{1,121}$=255.2, p<0.0001; stimulus×gender: $F_{1,121}$=8.7, p<0.01; stimulus×dose: $F_{3,121}$=4.3, p<0.01; stimulus genotype×dose: $F_{3,121}$=6.7, p<0.001; stimulus×gender×dose: $F_{3,121}$=3.3, p<0.05), time×spent in nose contact (dose effect: $F_{3,121}$=9.3, p<0.0001; genotype×dose: $F_{3,121}$=4.3, p<0.01; stimulus effect: $F_{1,121}$=329.0, p<0.0001; stimulus×genotype: $F_{1,121}$=4.1, p<0.05; stimulus×gender: $F_{1,121}$=7.6, p<0.01; stimulus×dose: $F_{3,121}$=10.3, p<0.0001; stimulus×genotype×dose: $F_{3,121}$=14.8, p<0.0001) and nose contact duration (dose effect: $F_{3,121}$=2.8, p<0.05; genotype×dose: $F_{3,121}$=3.3, p<0.05; stimulus effect: $F_{1,121}$=102.1, p<0.0001; stimulus×dose: $F_{3,121}$=11.3, p<0.0001; stimulus×genotype× dose: $F_{3,121}$=17.3, p<0.0001) to the level of wild-type animals in treated mutants.

In this test, bumetanide administered chronically restored the difference (preference for the mouse over the toy) in time spent in compartments (stimulus effect: $F_{1,55}$=36.5, p<0.0001; stimulus×genotype×dose: $F_{1,55}$=4.7, p<0.05) and number of nose contacts (stimulus effect: $F_{1,55}$=55.0, p<0.0001; stimulus×genotype×dose: $F_{1,55}$=8.9, p<0.01) in Oprm1$^{-/-}$ mice. In contrast, this treatment was unable to reverse the deficit in time spent in close contacts with the living mouse (genotype effect: $F_{1,55}$=16.2, p<0.001; dose effect: $F_{1,55}$=4.7, p<0.05; stimulus effect: $F_{1,55}$=34.5, p<0.0001; stimulus×genotype: $F_{1,55}$=29.4, p<0.0001; stimulus×genotype×dose: $F_{1,55}$=11.5, p<0.01) and their duration (genotype effect: $F_{1,55}$=7.5, p<0.01; dose effect: $F_{1,55}$=19.9, p<0.0001; stimulus×genotype: $F_{1,55}$=54.4, p<0.0001; stimulus×genotype×dose: $F_{1,55}$=9.3, p<0.01) in these animals (FIG. 3).

In conclusion, chronic bromide significantly improved social interaction and increased social preference in mu opioid receptor knockout mice. These beneficial effects on sociability were more significant in this mouse line than those of bumetanide at 0.5 mg/kg.

Figure 2:
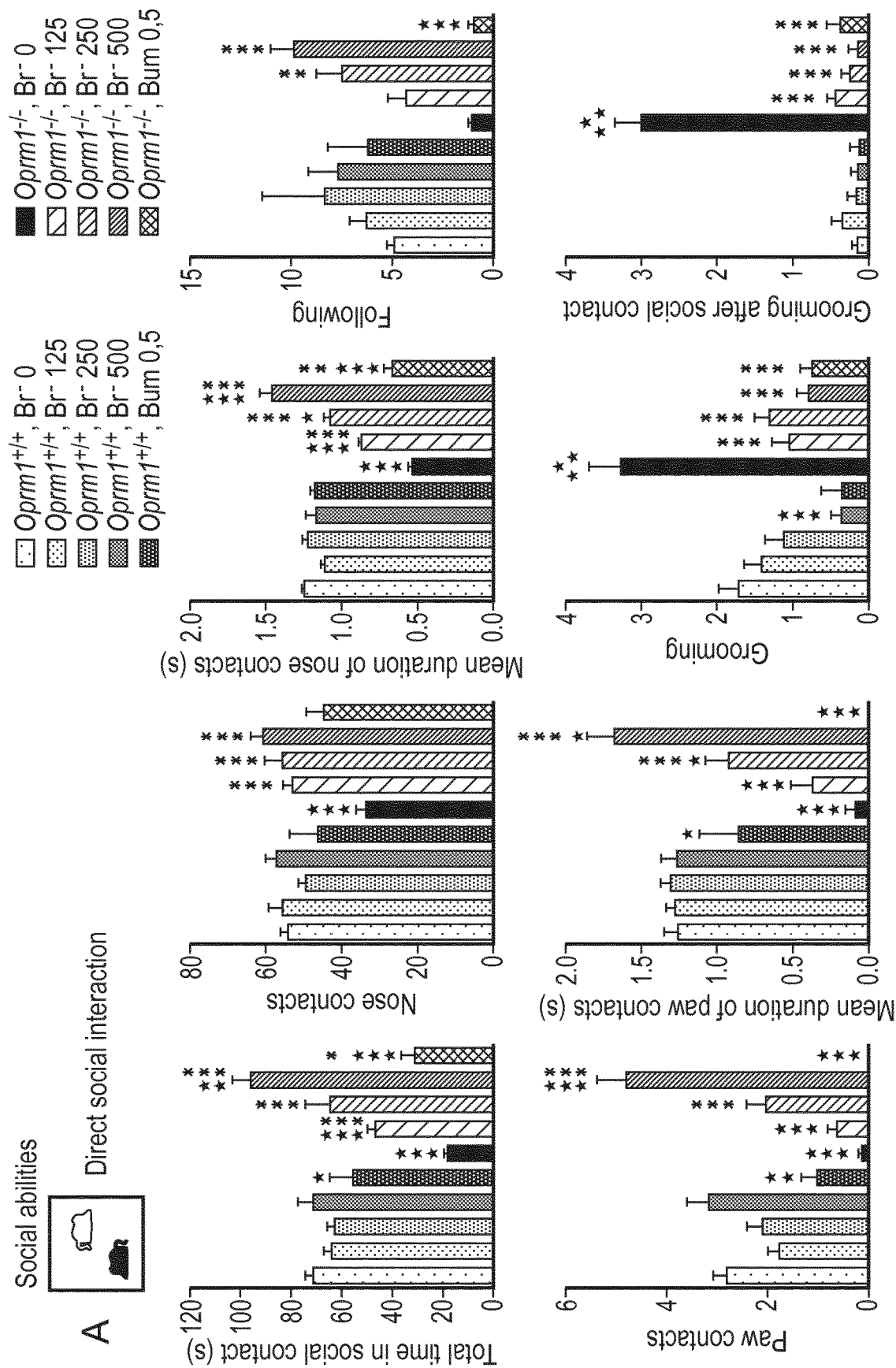
FIG. 2 shows the effects of chronic bromide treatment on social interaction test in mu opioid receptor null mice (Oprm1 null mice).
Figure 2:
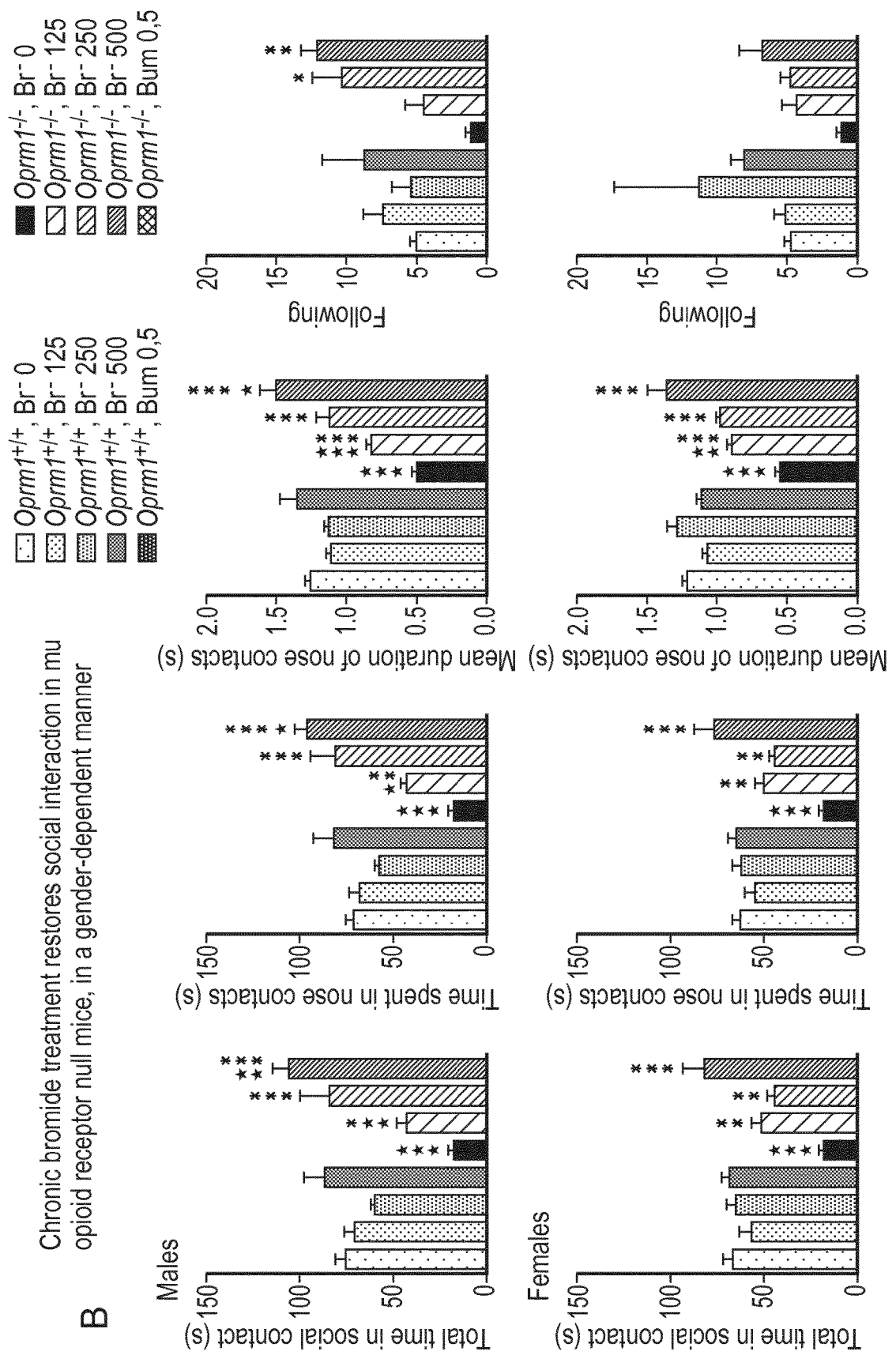

FIG. 2 shows the effects of chronic bromide treatment (125, 250 and 500 mg/kg) on the main behavioral parameters assessed in the direct social interaction test. (A) Chronic bromide administration increased the amount of time spent in social contact, the number and the mean duration of nose contacts, the number of following episodes, and the number and the mean duration of paw contacts in mu opioid receptor knockout mice, in a dose dependent manner. Conversely, chronic bromide reduced the number of grooming episodes, and especially those following a social contact in these animals. Under the same conditions, bumetanide (0.5 mg/kg) was only effective in reducing the number of grooming episodes, including those following a social contact. (B) Chronic bromide at the highest doses tested (250 mg/kg and 500 mg/kg) were more efficient in increasing the time spent in social and in nose contact, the mean duration of nose contacts and the number of following episodes in male than in female Oprm1$^{-/-}$ mice. Data are presented as mean±sem. Comparison to wild-type animals treated with vehicle: one star: $p<0.05$; two stars: $p<0.01$; three stars: $p<0.001$. Comparison to Oprm1 knockouts treated with vehicle: one asterisk: $p<0.05$; two asterisks: $p<0.01$; three asterisks: $p<0.001$ (three-way analysis of variance followed by Newman-Keules post-hoc test).

Figure 3:
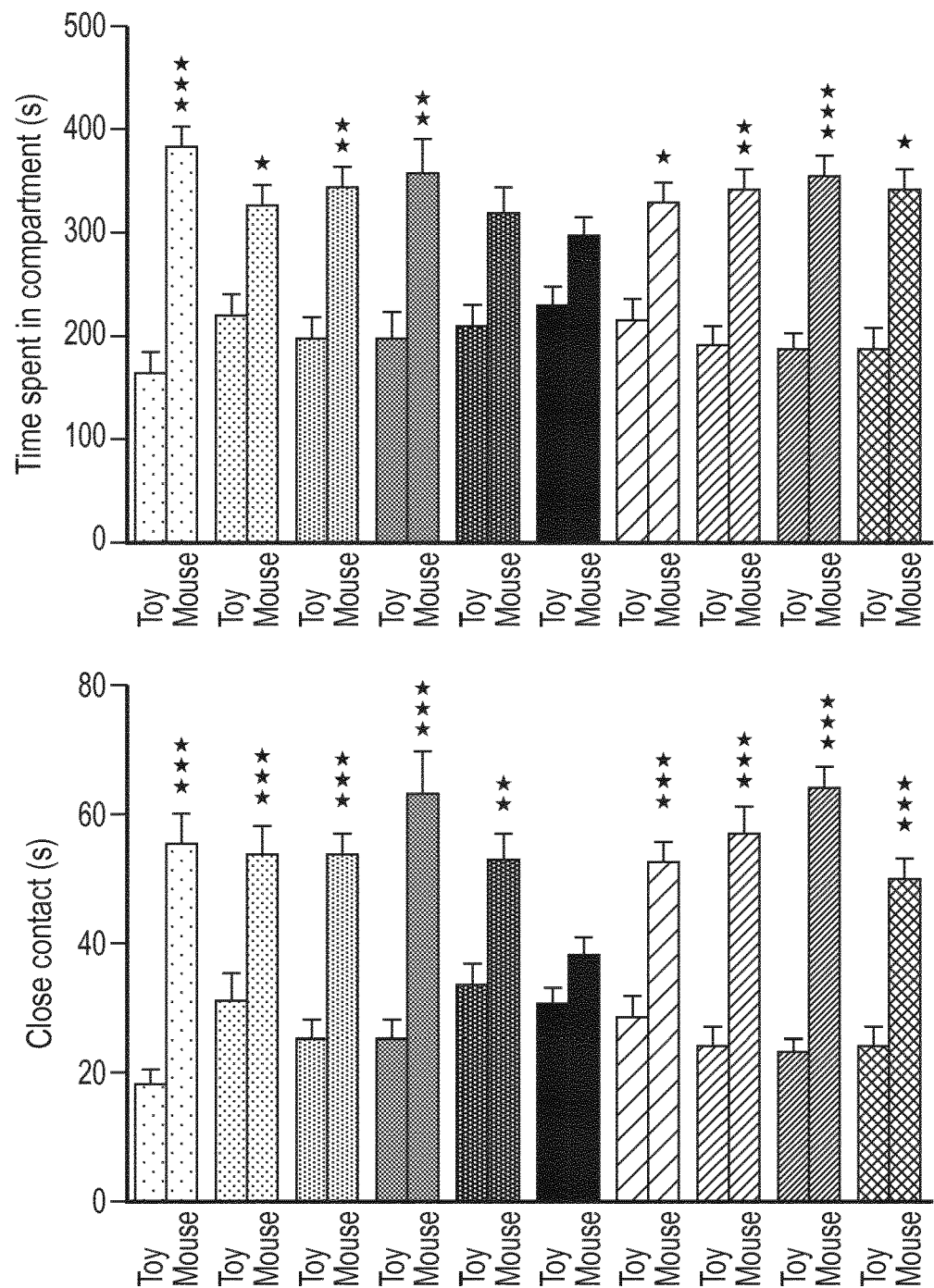
FIG. 3 shows the effect of chronic bromide administration on social preference in Oprm1 null mice.
Figure 3:
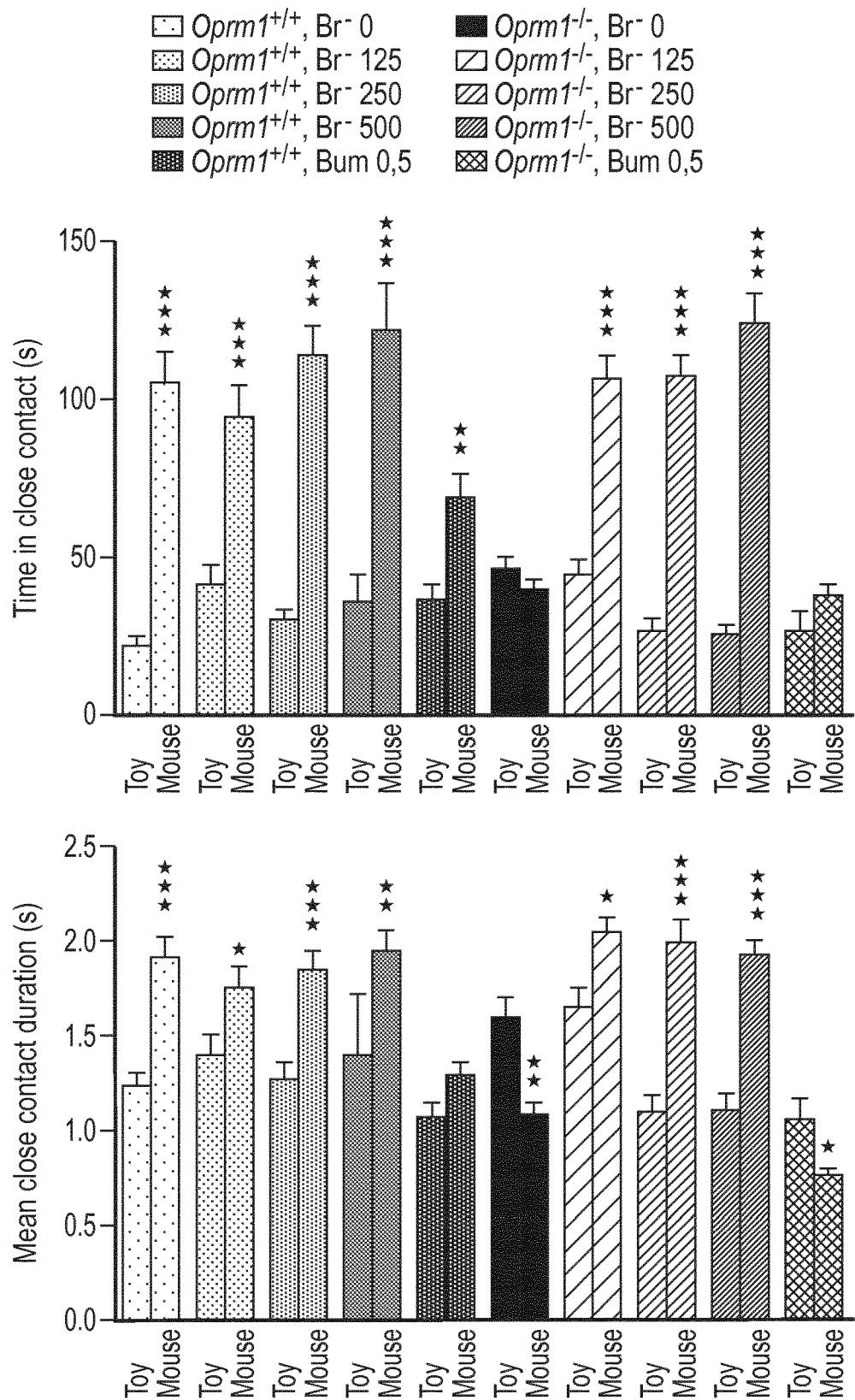

FIG. 3 shows the effects of chronic bromide treatment (125, 250 and 500 mg/kg) on the main behavioral parameters assessed in the three-chamber test of social preference. Chronic bromide treatment restored preference for the living mouse over the toy as illustrated by restored difference in time spent in the compartment containing the mouse, time spent in close contact with the mouse as well as number of close contacts and mean duration of close contacts with the mouse over the same parameters measured for the toy. Data are presented as mean±sem. Comparison mouse versus toy: one open star: $p<0.05$; two open stars: $p<0.01$; three open stars: $p<0.001$ (four-way analysis of variance followed by Newman-Keules post-hoc test).

Measures of Stereotyped Behaviour

We assessed the effects of chronic bromide treatment on repetitive behavior in mu opioid receptor knockout mice by scoring the presence of spontaneous motor stereotypies and by evaluating the pattern of exploration in the Y-maze in these mutants and their wild-type counterparts.

Chronic bromide treatment increased the number of rearing episodes in all animals in a dose-dependent manner (dose effect: $F_{3,121}=17.3$, $p<0.0001$). This treatment also dose-dependently increased the number of grooming episodes, but in wild-type animals only (genotype effect: $F_{1,121}=16.7$, $p<0.001$; dose effect: $F_{3,121}=4.1$, $p<0.01$; genotype×dose: $F_{3,121}=6.5$, $p<0.0001$). In contrast, bromide administration dose-dependently reduced the number of burying episodes (genotype effect: $F_{1,121}=12.8$, $p<0.001$; dose effect: $F_{3,121}=6.6$, $p<0.001$), the time spent burying (genotype effect: $F_{1,121}=15.5$, $p<0.001$; dose effect: $F_{3,121}=9.8$, $p<0.0001$) and the duration of burying events (dose effect: $F_{3,121}=4.2$, $p<0.0001$) in all animals. Bromide treatment dose-dependently increased the number of shakes in wild-type mice whereas it reduced their occurrence in mutant mice (dose effect: $F_{3,121}=3.7$, $p<0.05$; genotype×dose: $F_{3,121}=14.5$, $p<0.0001$). Finally, bromide normalized the number of circling episodes in Oprm1$^{-/-}$ mice (dose effect: $F_{3,121}=3.0$, $p<0.05$; genotype×dose: $F_{3,121}=9.1$, $p<0.0001$) to the level of wild-type animals. Thus, in larger cohorts than tested in Example 1, bromide treatment proved to efficiently reduce the occurrence of two motor stereotypies in mu opioid receptor null mice, namely shakes and circling behaviour.

Under the same conditions, chronic bumetanide treatment did not change the number of rearing and grooming episodes (no significant effects) in mutant or wild-type animals. This treatment, however, increased the number (dose effect: $F_{1,55}=5.3$, $p<0.05$), time spent in (dose effect: $F_{1,55}=7.7$, $p<0.01$) and not duration (no significant effect) of burying episodes in all mice. Finally, bumetanide efficiently suppressed stereotypic shakes (genotype effect: $F_{1,55}=10.0$, $p<0.01$; dose effect: $F_{1,55}=13.2$, $p<0.001$; genotype×dose: $F_{1,55}=26.4$, $p<0.0001$) and circling episodes (dose effect: $F_{1,55}=14.4$, $p<0.001$; genotype×dose: $F_{1,55}=23.9$, $p<0.0001$) in mutant animals (FIG. 4A). Thus bumetanide treatment efficiently relieved stereotypic behaviour in mice lacking the mu opioid receptor.

In the Y-maze exploration test, mutant mice performed as wild-type animals as regards rates of spontaneous alternation (no significant effect) and alternate arm returns, with bromide increasing the rate of the latter (dose effect: $F_{3,130}=3.6$, $p<0.05$). Mu opioid knockout mice, however, made significant more perseverative same arm returns when exploring the maze, and bromide efficiently reduced the number of these returns (genotype effect: $F_{1,130}=10.4$, $p<0.01$; dose effect: $F_{3,130}=5.3$, $p<0.001$).

In this test, bumetanide treatment (FIG. 4B) did not modify the rates of spontaneous alternation and alternate arm returns (no significant effect) in all animals, but reduced the excessive rate of same arm returns (genotype effect: $F_{1,65}=5.7$, $p<0.05$; genotype×dose: $F_{1,65}=10.3$, $p<0.01$) in Oprm1$^{-/-}$ mice.

In conclusion, chronic bromide demonstrated efficacy in reducing motor (shakes and circling) as well as cognitive (perseveration) stereotypies in mu opioid receptor knockout mice. Bumetanide treatment suppressed motor stereotypies and reduced cognitive stereotypies in the Y-maze.

Figure 4:
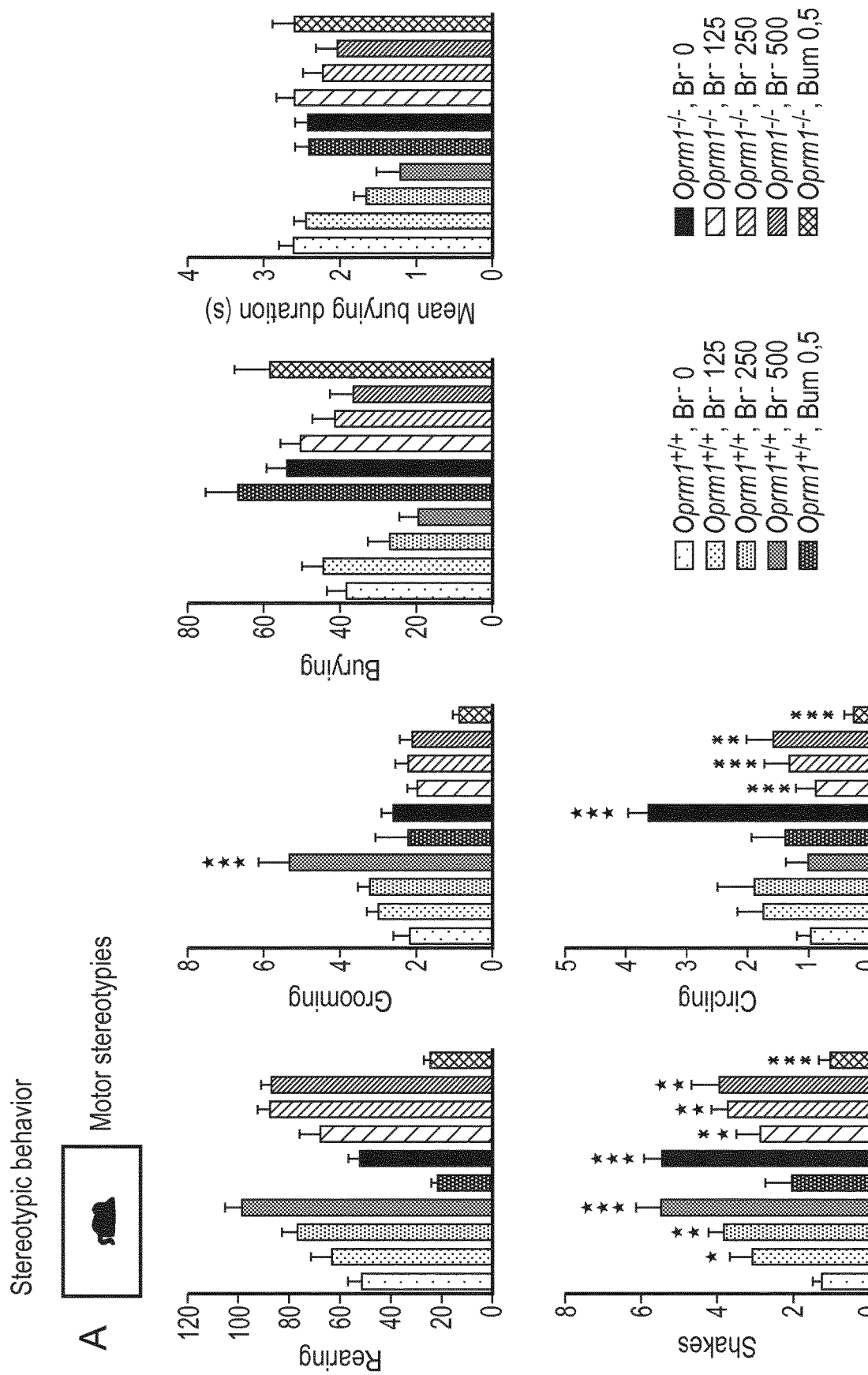
FIG. 4 shows the effect of chronic bromide administration on stereotypies and perseverative behaviour in Oprm1 null mice.
Figure 4:
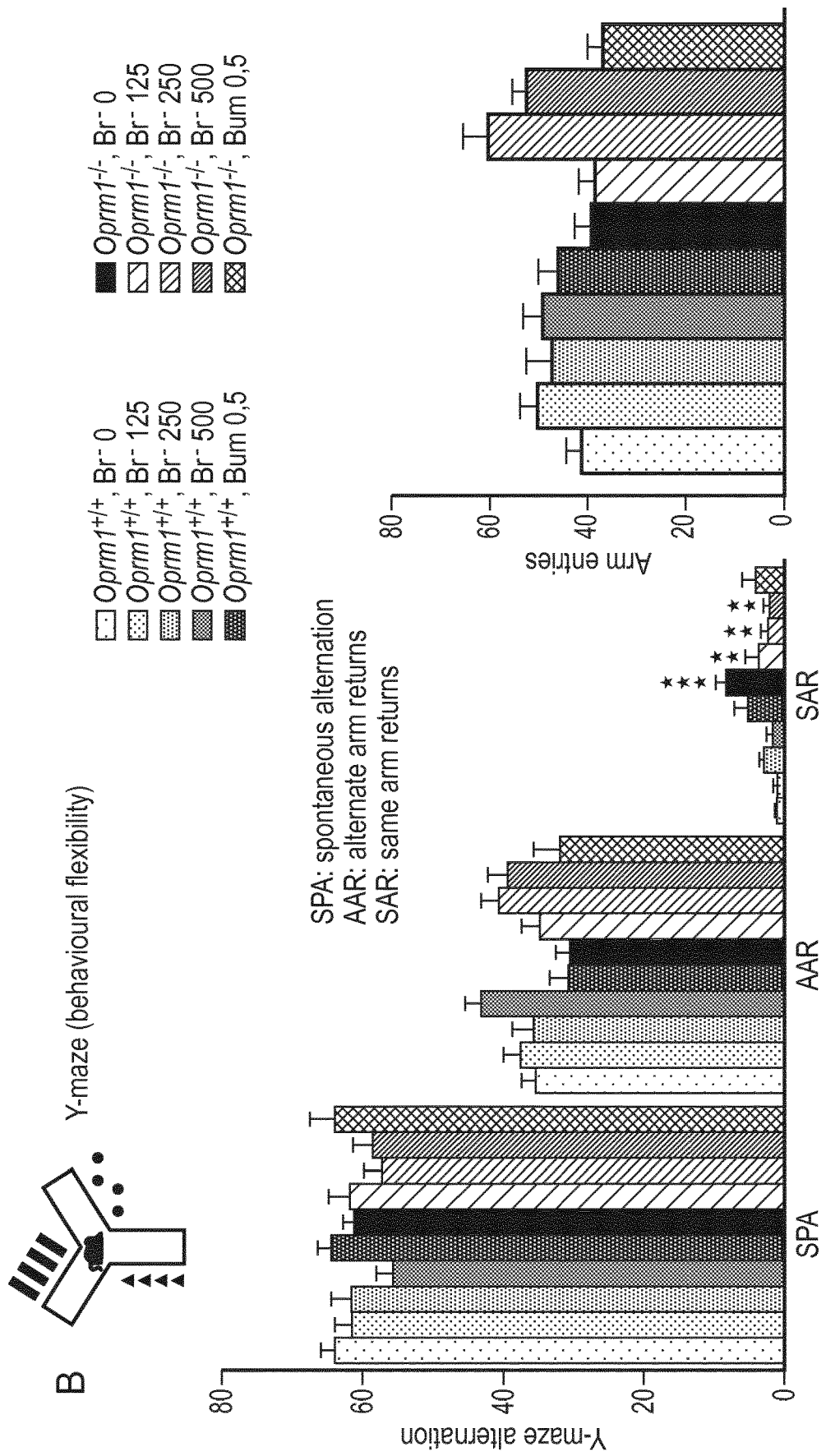

FIG. 4 shows the effects of chronic bromide treatment on stereotypic behaviors in mice lacking the Oprm1 gene. (A) Chronic bromide administration increased the number of rearing episodes in wild-type and knockout mice, increased grooming occurrence in wild-type animals only and dose dependently reduced the number of burying events, with no effect on their duration. Bromide decreased the number of stereotypic shakes and circling episodes in Oprm1$^{-/-}$ mice while it increased the former in Oprm1$^{+/+}$ animals. Bumetanide increased the number of burying events in moth mouse lines and efficiently suppressed shakes and circling episodes in knockout mice. (B) In the Y-maze, bromide treatment dose-dependently decreased the rate of same arm returns demonstrating efficiency in reducing cognitive stereotypies. Bumetanide similarly reduced this rate. Data are presented as mean±sem. Comparison to vehicle-treated wild-type animals: one star: $p<0.05$; two stars: $p<0.01$; three stars: $p<0.001$; comparison to Oprm1 knockouts treated with vehicle: one asterisk: $p<0.05$; two asterisks: $p<0.01$; three asterisks: $p<0.001$ (three-way analysis of variance followed by Newman-Keules post-hoc test).

Measures of Anxiety

Figure 5:
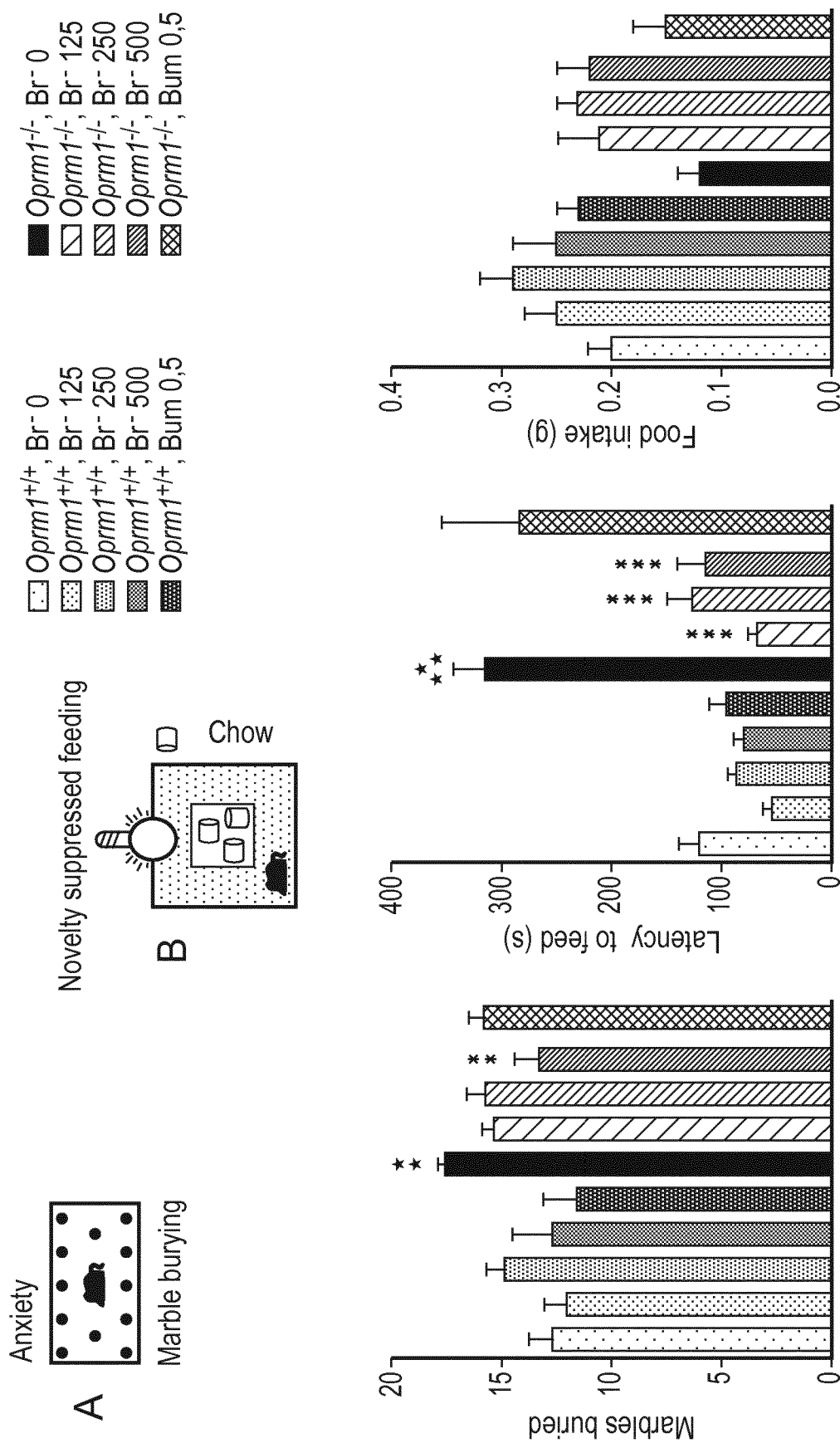
FIG. 5 shows the effect of chronic bromide administration on anxiety in Oprm1 null mice.

We evaluated the effects of chronic bromide administration on anxiety levels using two tests, the marble burying test and the novelty-suppressed feeding test (FIG. 5). Oprm1$^{-/-}$ mice buried more marbles than wild-type animals in the marble burying test, and chronic bromide treatment reduced this burying (genotype effect: $F_{1,121}=14.8$, $p<0.0001$; dose effect: $F_{3,121}=3.2$, $p<0.05$). Bumetanide did not significantly modify this parameter (genotype effect: $F_{1,55}=19.6$, $p<0.0001$).

In the novelty-suppressed feeding test, all three doses of bromide efficiently reduced the feeding latency to wild-type level (genotype effect: $F_{1,121}=28.3$, $p<0.0001$; gender effect: $F_{1,121}=10.0$, $p<0.01$; dose effect: $F_{3,121}=3.2$, $p<0.05$; genotype×dose: $F_{3,121}=11.11$ $p<0.0001$).

Chronic bromide increased food intake back in the home cage in wild-type and mutant mice (genotype effect: $F_{1,121}=5.3$, $p<0.05$; dose effect: $F_{3,121}=6.0$, $p<0.001$; gender×dose: $F_{3,121}=4.2$, $p<0.01$). Chronic bumetanide treatment did not modify significantly these parameters (feeding latency: $F_{1,65}=29.3$, $p<0.0001$; food intake: $F_{1,65}=10.7$, $p<0.01$).

Together, these data indicate that chronic bromide efficiently reduced behavioural signs of anxiety in mice lacking mu opioid receptors. Bumetanide did not show effects at the dose tested.

FIG. 5 depicts the effects of chronic bromide treatment on measures of anxiety in Oprm1$^{-/-}$ mice and their Oprm1$^{+/+}$ controls. (A) In the marble burying test, bromide treatment diminished the number of buried marbles in mutant animals, most significantly at the dose of 500 mg/kg. (B) In the novelty-suppressed feeding test, mu opioid receptor null mice displayed a markedly increased latency to feed on the pellets, and chronic bromide administration normalized this measure to wild-type levels independently from the dose. Bromide increased food intake when mice where returned to their home cage, whatever their genotype. Data are presented as mean±sem. Comparison to wild-type animals treated with vehicle: one star: $p<0.05$; two stars: $p<0.01$; three stars: $p<0.001$. Comparison to Oprm1 knockouts treated with vehicle: one asterisk: $p<0.05$; two asterisks: $p<0.01$; three asterisks: $p<0.001$ (three-way analysis of variance followed by Newman-Keules post-hoc test).

We chose the intermediate dose of 250 mg/kg of bromide that demonstrated efficacy in relieving most autistic-like symptoms in mu opioid receptor null mice to test in two more murine models of autism: mice lacking the Fmr1 and the Shank3 gene.

Fmr1$^{-/-}$ Mice

Statistical power in these experiments was not sufficient to test gender effects.

Measures of Sociability

In the direct social interaction test, chronic bromide at 250 mg/kg normalized the time spent in social contact (genotype effect: $F_{1,30}=31.8$, $p<0.0001$; dose effect: $F_{1,30}=40.6$, $p<0.0001$; genotype×dose: $F_{1,30}=30.2$, $p<0.0001$) and in nose contact (genotype effect: $F_{1,30}=30.5$, $p<0.0001$; dose effect: $F_{1,30}=37.3$, $p<0.0001$; genotype×dose: $F_{1,30}=28.1$, $p<0.0001$), the duration of nose contacts (genotype effect: $F_{1,30}=112.1$, $p<0.0001$; dose effect: $F_{1,30}=48.9$, $p<0.0001$; genotype×dose: $F_{1,30}=49.5$, $p<0.0001$), the number of following episodes (dose effect: $F_{1,30}=9.9$, $p<0.01$; genotype× dose: $F_{1,30}=13.7$, $p<0.001$) and the number of (dose effect: $F_{1,30}=14.4$, $p<0.001$; genotype×dose: $F_{1,30}=10.7$, $p<0.01$), time spent in (genotype effect: $F_{1,30}=9.9$, $p<0.05$; dose effect: $F_{1,30}=17.8$, $p<0.001$; genotype×dose: $F_{1,30}=10.6$, $p<0.01$) and duration (genotype effect: $F_{1,30}=81.4$, $p<0.0001$; dose effect: $F_{1,30}=30.9$, $p<0.0001$; genotype× dose: $F_{1,30}=27.1$, $p<0.0001$) of paw contacts that were deficient in Fmr1 mutants. Moreover, bromide treatment reduced the excessive number of grooming episodes (genotype effect: $F_{1,30}=8.6$, $p<0.01$; dose effect: $F_{1,30}=6.6$, $p<0.05$; genotype×dose: $F_{1,30}=10.9$, $p<0.001$) and notably those occurring after a social contact (genotype effect: $F_{1,30}=47.7$, $p<0.0001$; dose effect: $F_{1,30}=22.4$, $p<0.0001$; genotype×dose: $F_{1,30}=30.1$, $p<0.0001$) in knockout mice.

In the three-chamber test, bromide treatment had no significant effect on neither preferential time spent in the compartment with the mouse (stimulus effect: $F_{1,30}=6.1$, $p<0.05$) or number of close contacts with the mouse (stimulus effect: $F_{1,30}=17.2$, $p<0.001$) in knockout or wild-type animals; however this treatment increased preference in time spent in close contact with the mouse versus the toy (dose effect: $F_{1,30}=12.3$, $p<0.01$; stimulus effect: $F_{1,30}=19.4$, $p<0.001$; stimulus×dose: $F_{1,30}=6.1$, $p<0.05$) and duration of such close contacts (dose effect: $F_{1,30}=5.7$, $p<0.05$; stimulus effect: $F_{1,30}=4.6$, $p<0.05$) that were markedly reduced in Fmr1 null animals.

Together, these results indicate that bromide treatment efficiently restores sociability parameters in Fmr1 knockout mice.

Figure 6:
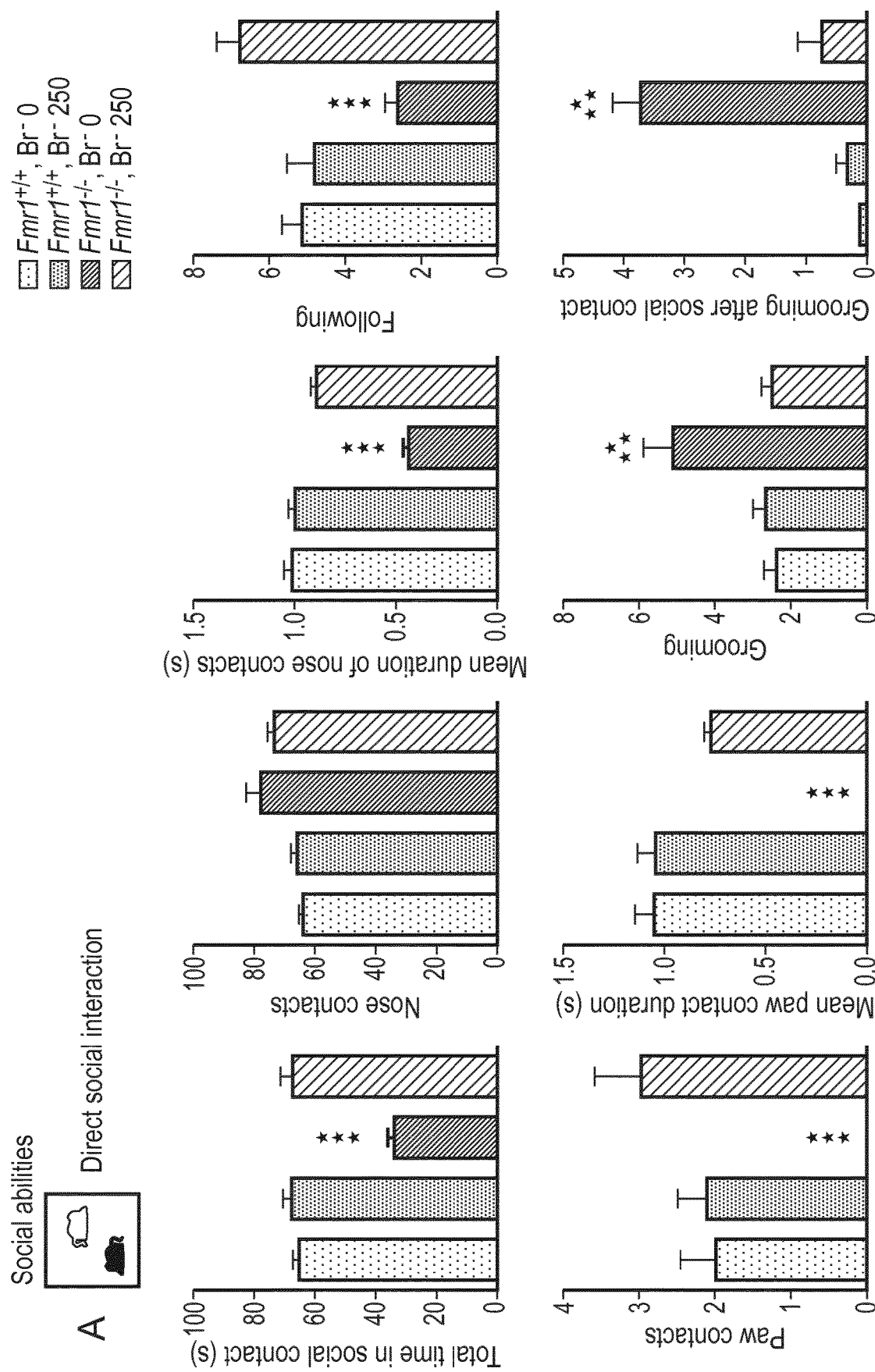
FIG. 6 shows the effect of chronic bromide administration on social interaction in Fmr1 null mice.
Figure 6:
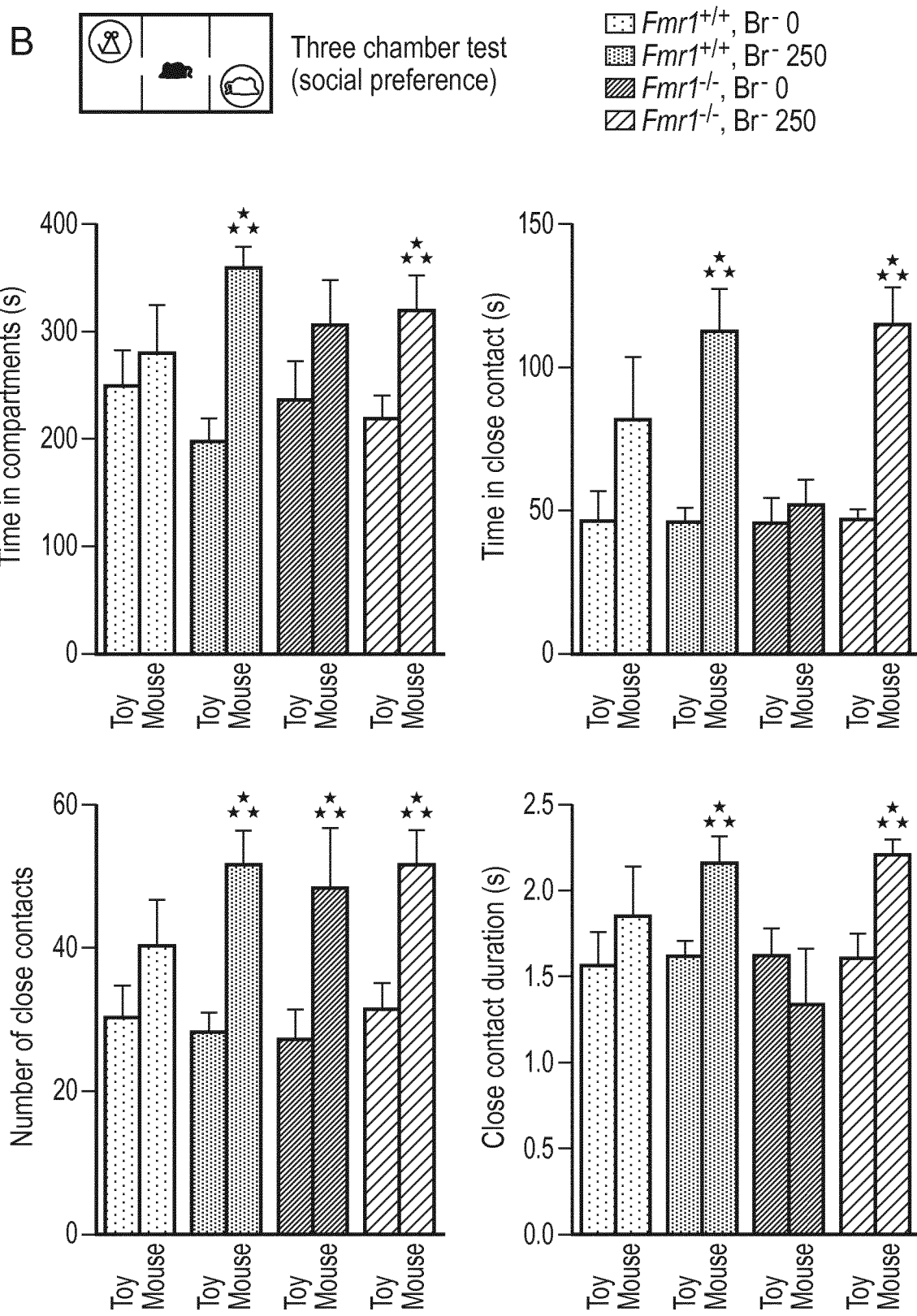

FIG. 6 shows the effects of chronic bromide treatment (250 mg/kg) on social abilities in mice lacking the Fmr1 gene. (A) Chronic bromide administration normalized the time spent in social contact, the mean duration of nose contacts, the number of following episodes, and the number and mean duration of paw contacts in Fmr1 knockout mice to wild-type levels. In contrast, chronic bromide reduced the number of grooming episodes, and especially those following a social contact in these animals. (B) In the three-chamber test, chronic bromide restored preference for time spent in close contact with the mouse versus the toy and mean duration of these close contacts. Data are presented as mean±sem. Comparison to wild-type animals treated with vehicle: plain stars-one star: $p<0.05$; two stars: $p<0.01$; three stars: $p<0.001$. Comparison mouse versus toy: open stars-three stars: $p<0.001$ (two- or three-way analysis of variance followed by Newman-Keules post-hoc test).

Measures of Stereotyped Behaviour

In 10-min direct observation, we detected no effect of genotype or bromide treatment in Fmr1 knockout and their wild-type controls on the number of rearing, grooming or burying episodes (no significant effect). However, bromide administration reduced the time spent burying (dose effect: $F_{1,30}=5.5$, $p<0.05$) and the duration of burying events (dose effect: $F_{1,30}=4.9$, $p<0.05$) in all animals. Finally, bromide normalized the number of shakes (genotype×dose: $F_{1,30}=19.6$, $p<0.001$) and circling episodes (genotype effect: $F_{1,30}=7.3$, $p<0.05$; dose effect: $F_{1,30}=6.1$, $p<0.05$; genotype× dose: $F_{1,30}=11.9$, $p<0.01$) in Fmr1$^{-/-}$ mice to the level of wild-type animals. Thus bromide treatment efficiently reduced the occurrence of motor stereotypies in Fmr1 knockout mice.

In the Y-maze exploration test, mutant mice performed as wild-type animals as regards rates of spontaneous alternation and alternate arm returns (no significant effects). Fmr1 knockout mice, however, made significant more perseverative same arm returns when exploring the maze, and bromide administration efficiently reduced the number of these returns (genotype effect: $F_{1,30}=49.7$, $p<0.0001$; dose effect: $F_{1,30}=49.7$, $p<0.0001$; genotype×dose: $F_{1,30}=58.0$, $p<0.0001$).

These data demonstrate that bromide treatment relieves motor and cognitive stereotypies in Fmr1 knockout mice.

Figure 7:
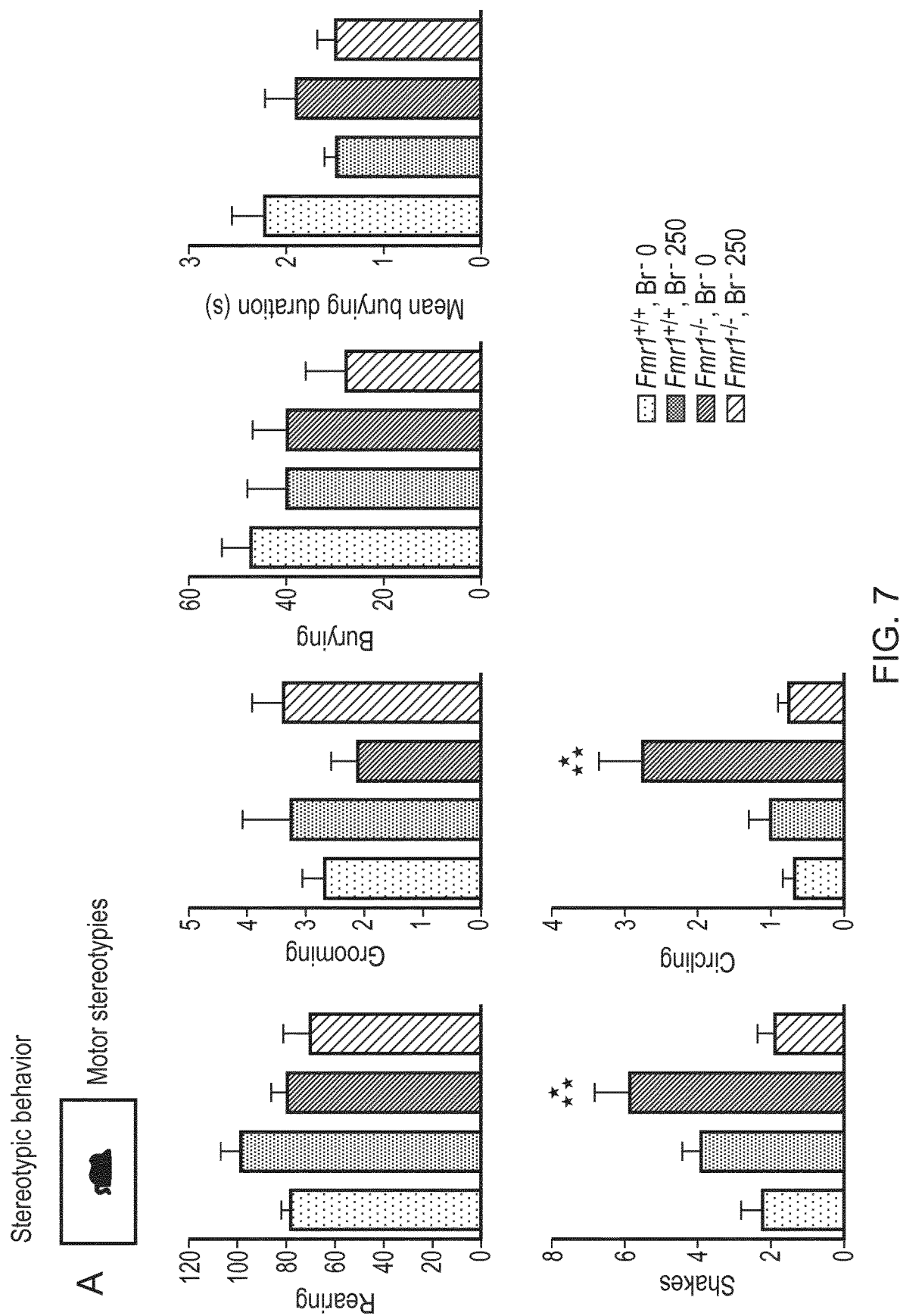
FIG. 7 shows the effect of chronic bromide administration on stereotypies and perseverative behaviour in Fmr1 null mice.
Figure 7:
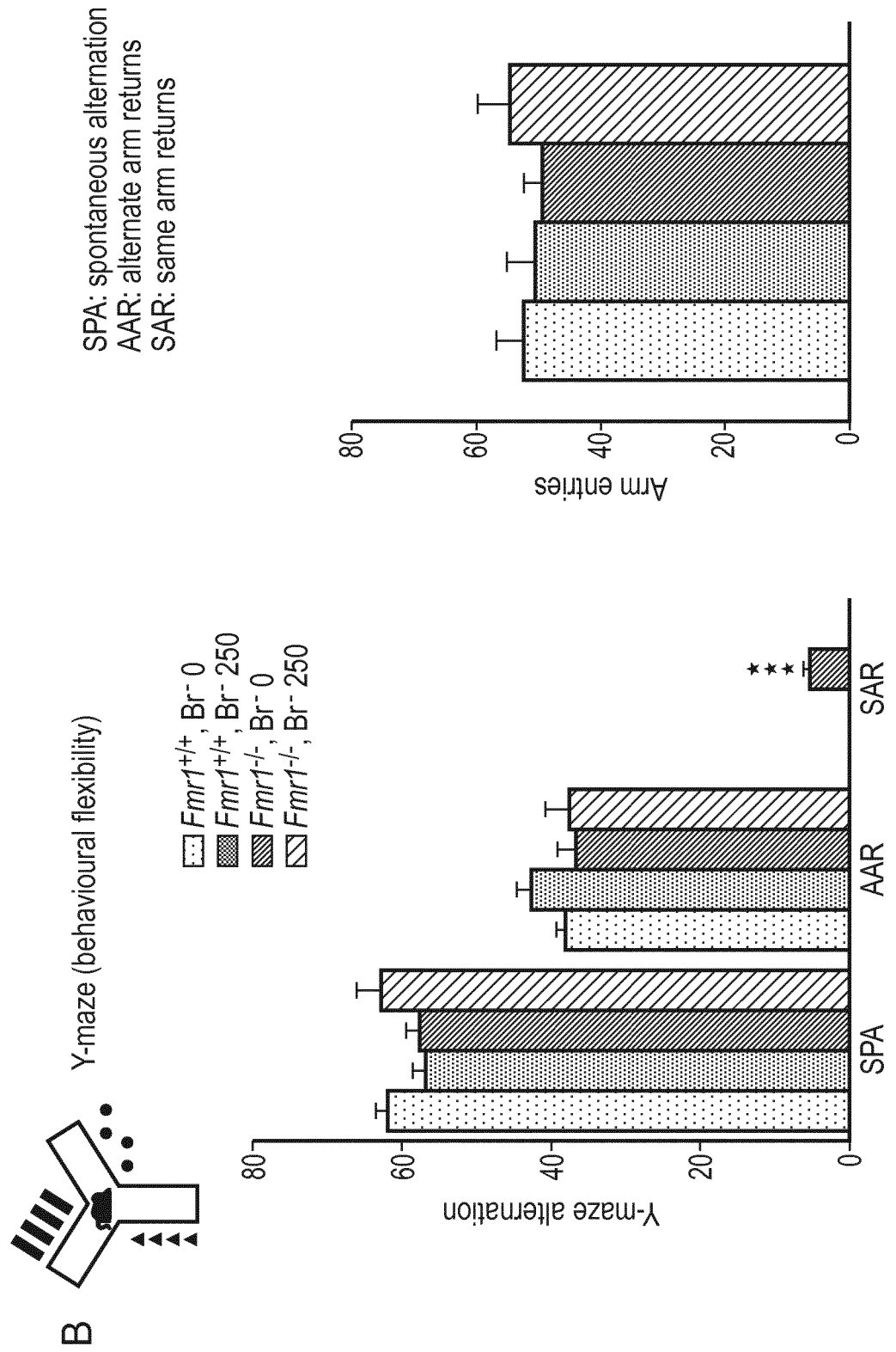

FIG. 7 illustrates the effects of chronic bromide treatment on stereotypic behaviors in Fmr1 knockout animals. (A) Chronic bromide administration reduced the mean duration of burying episodes in Fmr1 mutants and their wild-type controls. Furthermore, this treatment reduced the number of stereotyped shakes and circling episodes to wild-type levels in knockout mice. (B) In the Y-maze, bromide treatment suppressed perseverative same arm returns in Fmr1$^{-/-}$ mice. Data are presented as mean±sem. Comparison to vehicle-treated wild-type group: one star: $p<0.05$; two stars: $p<0.01$; three stars: $p<0.001$ (two-way analysis of variance followed by Newman-Keules post-hoc test).

Measures of Anxiety

We detected no behavioural difference between Fmr1$^{-/-}$ and Fmr1$^{+/+}$ mice in the marble burying test; chronic bromide treatment reduced the number of marbles buried in both of these lines (dose effect: $F_{1,30}=7.3$, $p<0.05$).

In the novelty-suppressed feeding test, bromide administration reduced the feeding latency to wild-type level in Fmr1 mutants (genotype×dose: $F_{1,30}$=6.7, p<0.05). This treatment did not modify food intake back in the home cage (no significant effect). Together, these data show that bromide can reduce exacerbated anxiety in mice lacking the Fmr1 gene.

Figure 8:
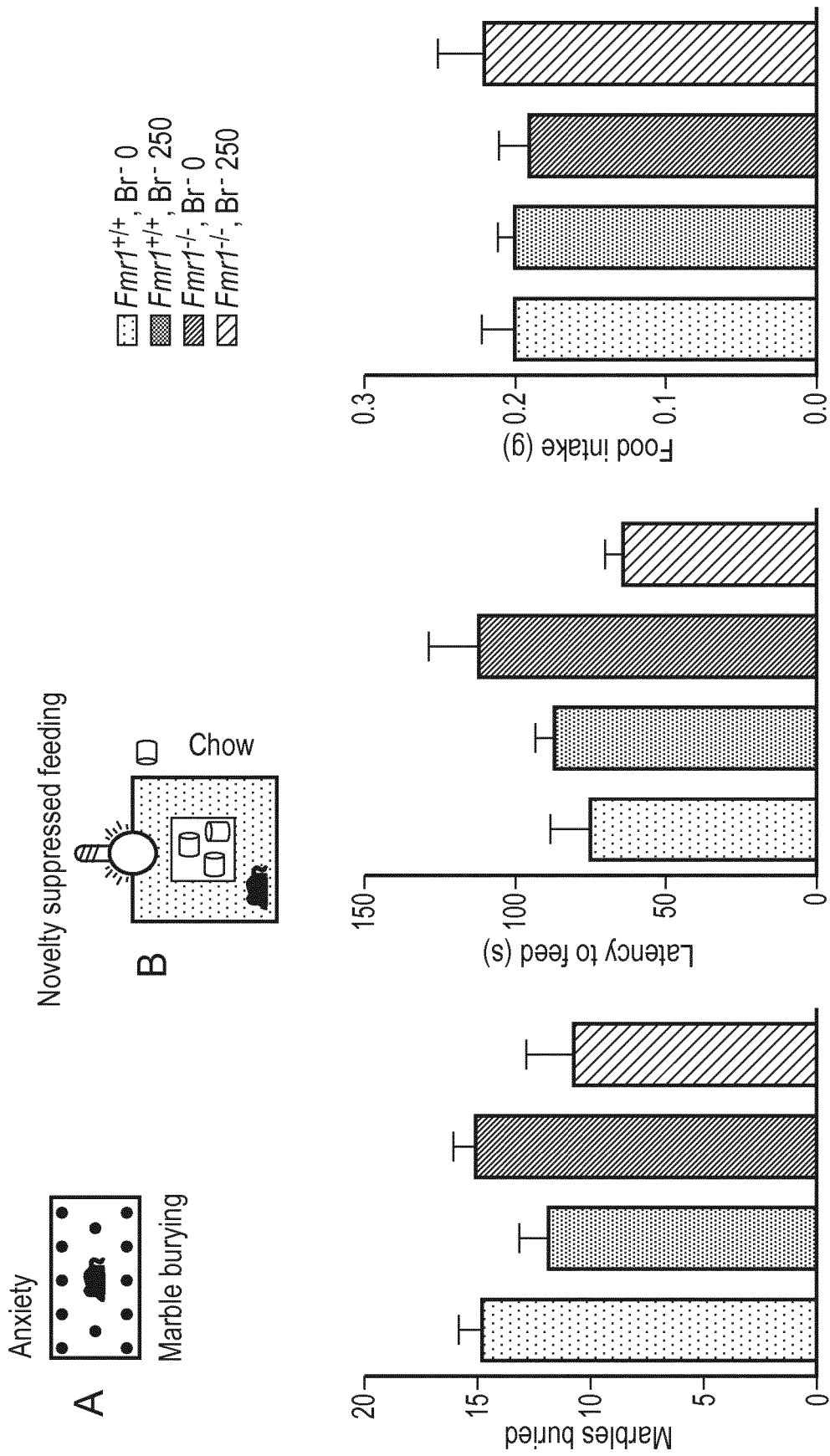
FIG. 8 shows the effect of chronic bromide administration on anxiety in Fmr1 null mice.

FIG. 8 shows the effects of chronic bromide treatment on anxiety levels in Fmr1 knockout mice. (A) In the marble burying test, bromide treatment reduced the number of marbles buried in mutant nd wild-type mice. (B) In the novelty-suppressed feeding test, bromide administration decreased the latency to feed in Fmr1$^{-/-}$ mice to wild-type level. Data are presented as mean±sem. Comparison to vehicle-treated wild-type group: one star: p<0.05 (two-way analysis of variance followed by Newman-Keules post-hoc test).

Shank3B$^{-/-}$ Mice

Statistical power in these experiments was not sufficient to test gender effects.

Measures of Sociability

In the direct social interaction test, chronic bromide at 250 mg/kg restored to wild-type levels the time spent in social contact (genotype effect: $F_{1,28}$=46.2, p<0.0001; dose effect: $F_{1,28}$=74.0, p<0.0001; genotype×dose: $F_{1,28}$=47.0, p<0.0001) and in nose contact (genotype effect: $F_{1,28}$=45.4, p<0.0001; dose effect: $F_{1,28}$=63.0, p<0.0001; genotype×dose: $F_{1,28}$=38.7, p<0.0001), the number (genotype effect: $F_{1,28}$=19.9, p<0.001; dose effect: $F_{1,28}$=37.7, p<0.0001; genotype×dose: $F_{1,28}$=21.7, p<0.0001) and duration of nose contacts (genotype effect: $F_{1,28}$=99.4, p<0.0001; dose effect: $F_{1,28}$=82.7, p<0.0001; genotype×dose: $F_{1,28}$=73.0, p<0.0001), the number of following episodes (dose effect: $F_{1,28}$=10.6, p<0.01; genotype×dose: $F_{1,28}$=11.8, p<0.01) and the number of (dose effect: $F_{1,28}$=14.8, p<0.001; genotype×dose: $F_{1,28}$=18.0, p<0.001), time spent in (dose effect: $F_{1,28}$=12.8, p<0.01; genotype×dose: $F_{1,28}$=12.9, p<0.01) and duration (genotype effect: $F_{1,28}$=19.0, p<0.001; dose effect: $F_{1,28}$=48.0, p<0.0001; genotype×dose: $F_{1,28}$=23.2, p<0.0001) of paw contacts in Shank3B null mice. Moreover, bromide treatment reduced the excessive number of grooming episodes (genotype effect: $F_{1,28}$=41.8, p<0.0001; genotype×dose: $F_{1,28}$=7.1, p<0.05) specially those occurring after a social contact (genotype effect: $F_{1,28}$=40.1, p<0.0001; dose effect: $F_{1,28}$=32.1, p<0.0001; genotype×dose: $F_{1,28}$=25.0, p<0.0001) scored in mutants.

In the three-chamber test, bromide treatment had no significant effect on neither preferential time spent in the compartment (genotype effect: $F_{1,28}$=11.1, p<0.01; stimulus effect: $F_{1,28}$=9.2, p<0.01) or number of close contacts (stimulus effect: $F_{1,28}$=37.4, p<0.0001) with the mouse versus the toy; however chronic bromide administration increased preference in time spent in close contact with the mouse versus the toy (stimulus effect: $F_{1,28}$=58.9, p<0.0001; stimulus×dose: $F_{1,28}$=5.3, p<0.05; stimulus×dose×genotype: $F_{1,28}$=4.5, p<0.05) and duration of such close contacts (genotype×dose: $F_{1,28}$=4.8, p<0.05; stimulus effect: $F_{1,28}$=56.3, p<0.0001; stimulus×dose: $F_{1,28}$=10.2, p<0.01; stimulus×dose×genotype: $F_{1,28}$=26.9, p<0.0001).

Together, these results indicate that bromide treatment efficiently restores sociability parameters in Shank3B knockout mice.

Figure 9:
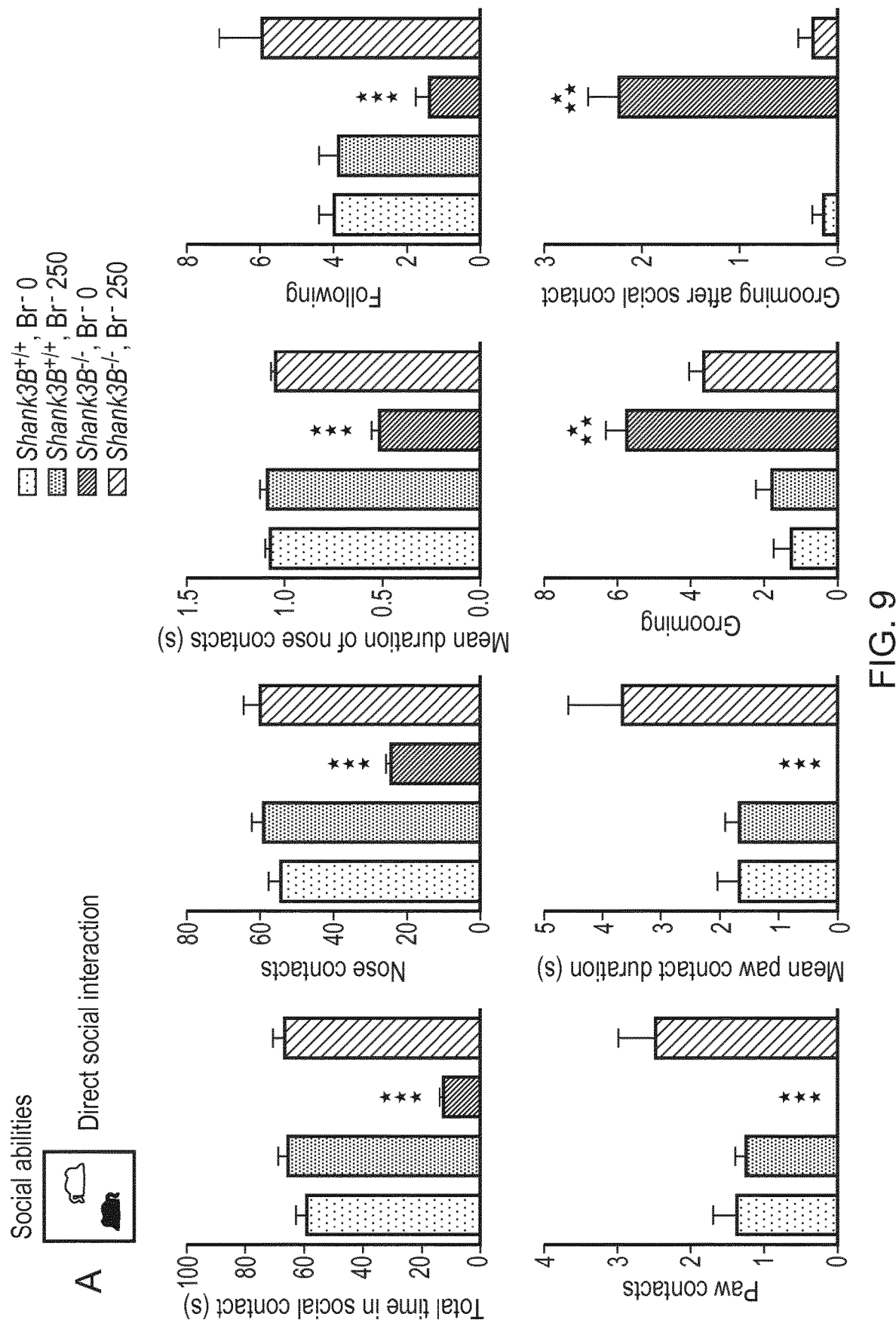
FIG. 9 shows the effect of chronic bromide administration on social interaction in Shank3B null mice.
Figure 9:
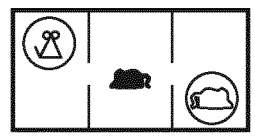
Figure 9:
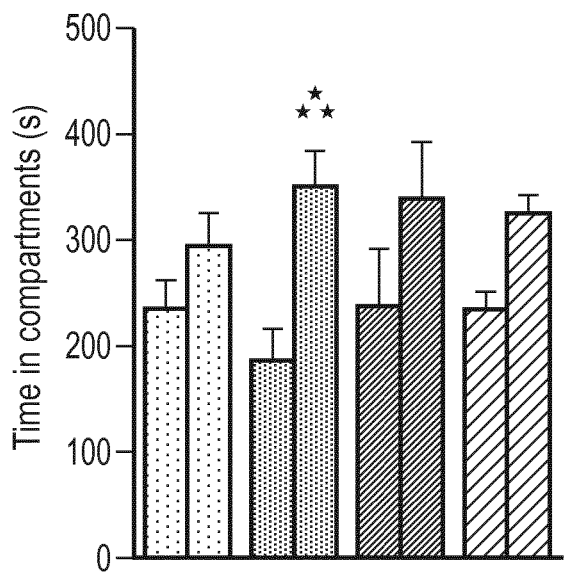
Figure 9:
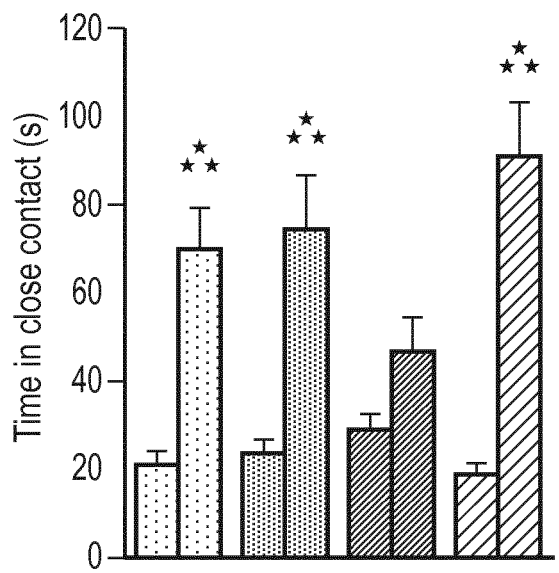
Figure 9:
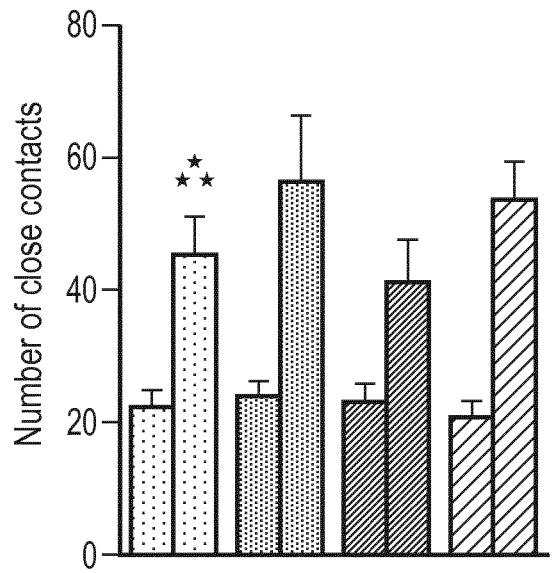
Figure 9:
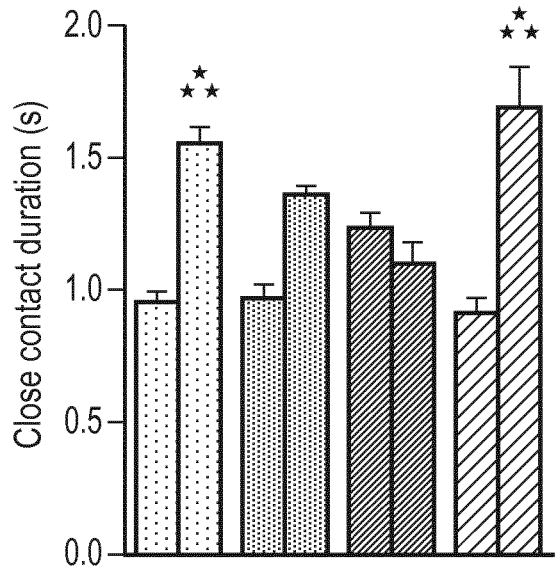

FIG. 9 illustrates the effects of chronic bromide treatment (250 mg/kg) on social abilities in mice lacking the Shank3B gene. (A) Chronic bromide administration reduced the time spent in social contact, the number and mean duration of nose contacts, the number of following episodes, and the number and mean duration of paw contacts in Shank3B knockout mice to wild-type levels. Moreover, chronic bromide reduced the number of grooming episodes, and especially those following a social contact in these animals. (B) In the three-chamber test, chronic bromide restored preference for time spent in close contact with the mouse versus the toy and mean duration of these close contacts. Data are presented as mean±sem. Comparison to wild-type animals treated with vehicle: plain stars-three stars: p<0.001. Comparison mouse versus toy: open stars-three stars: p<0.001 (two- or three-way analysis of variance followed by Newman-Keules post-hoc test).

Measures of Stereotyped Behaviour

Shank3B$^{-/-}$ mice and their wild-type controls displayed the same number of rearing episodes with no effect of bromide treatment (no significant effect) during a 10-min scoring. Knockout animals buried less during the test, and bromide had no significant influence on this parameter (genotype effect: $F_{1,28}$=45.4, p<0.0001). In contrast, the number of grooming episodes, shakes and circling episodes were increased in Shank3B mutants and bromide treatment normalized these measures to control levels (grooming: genotype effect: $F_{1,28}$=24.3, p<0.0001; dose effect: $F_{1,28}$=7.8, p<0.01; genotype×dose: $F_{1,28}$=10.2, p<0.01; shakes: genotype effect: $F_{1,28}$=24.8, p<0.0001; dose effect: $F_{1,28}$=6.0, p<0.05; genotype×dose: $F_{1,28}$=5.3, p<0.05; circling: genotype effect: $F_{1,28}$=24.2, p<0.0001; dose effect: $F_{1,28}$=18.0, p<0.001; genotype×dose: $F_{1,28}$=48.4, p<0.0001). Thus bromide treatment efficiently reduced the occurrence of motor stereotypies in Shank3B knockout mice.

In the Y-maze exploration test, Shank3B mutant mice displayed a severe deficit in the rates of spontaneous alternation that was rescued by bromide administration (genotype effect: $F_{1,28}$=4.3, p<0.05; dose effect: $F_{1,28}$=8.1, p<0.01; genotype×dose: $F_{1,28}$=9.4, p<0.01)

The rate of alternate arm returns was not modified by genotype and treatment (no significant effects). Finally, Shank3B knockout mice showed markedly elevated rates of perseverative same arm returns when exploring the maze, and bromide administration normalized this measure to wild-type levels (genotype effect: $F_{1,28}$=42.7, p<0.0001; dose effect: $F_{1,28}$=61.1, p<0.0001; genotype×dose: $F_{1,28}$=47.5, p<0.0001).

These data demonstrate that bromide treatment relieves motor and cognitive stereotypies in Shank3B knockout mice.

Figure 10:
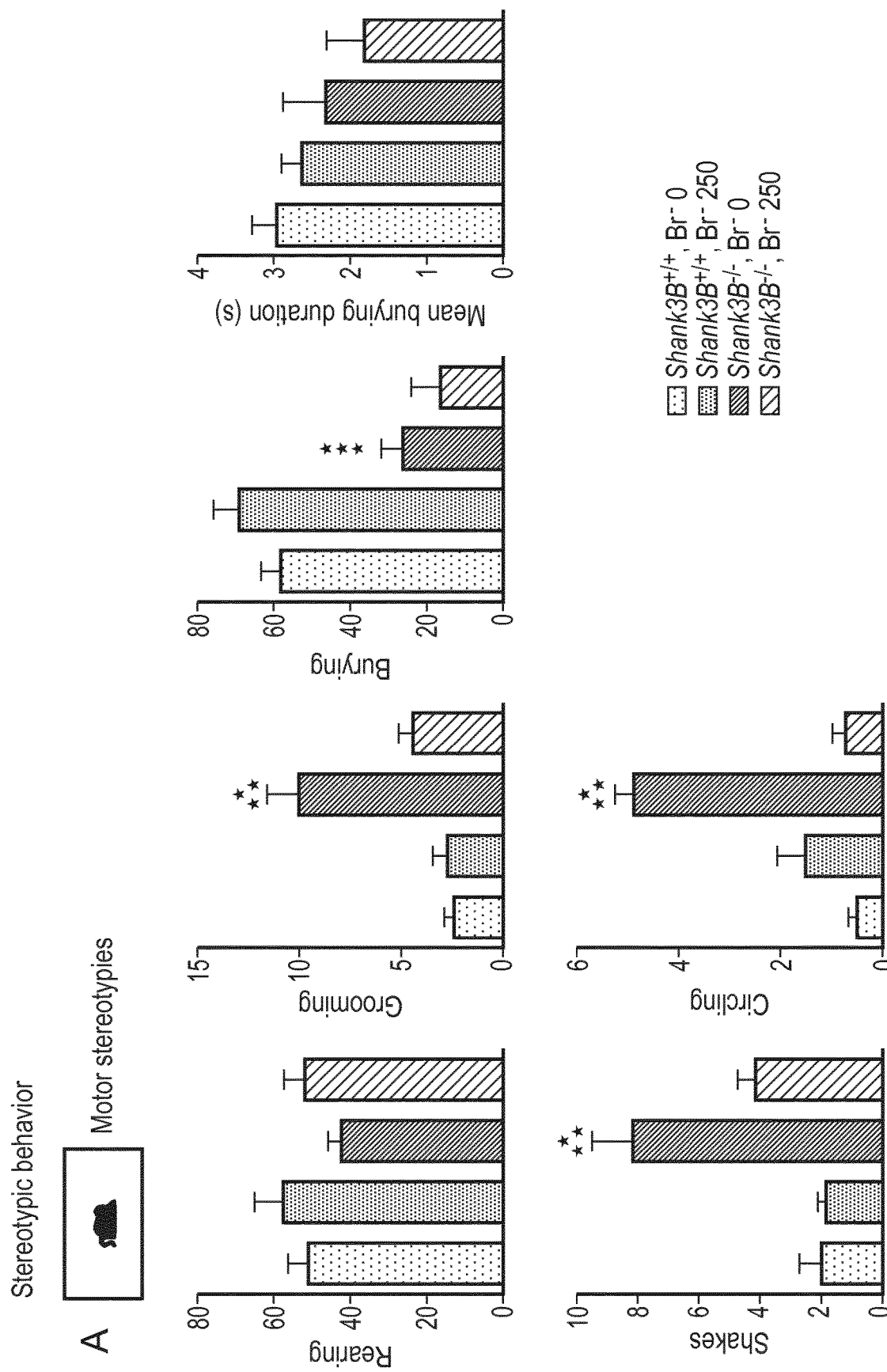
FIG. 10 shows the effect of chronic bromide administration on stereotypies and perseverative behaviour in Shank3B null mice.
Figure 10:
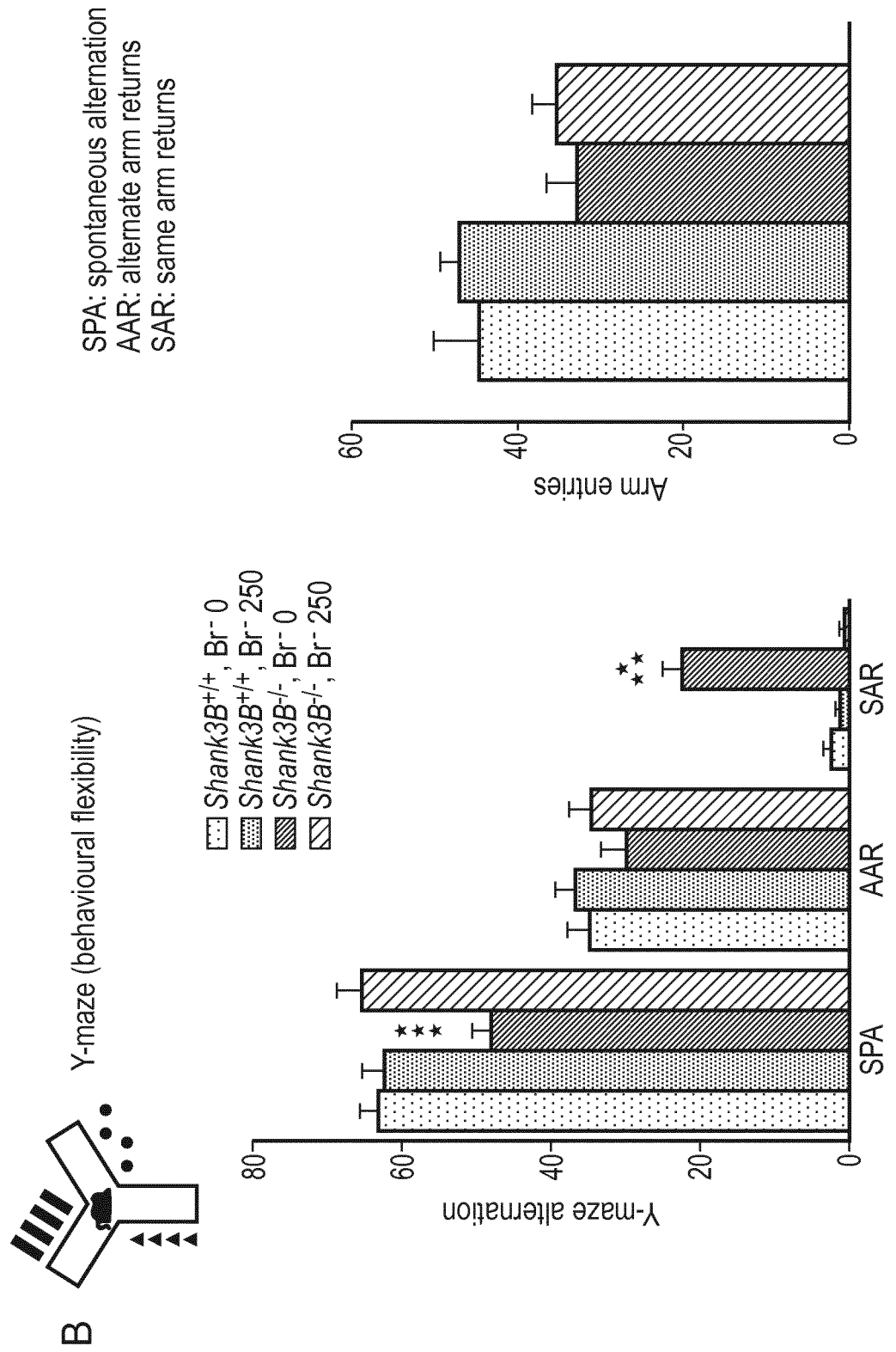

FIG. 10 shows the effects of chronic bromide treatment on stereotypic behaviors in Shank3B knockout animals. (A) Chronic bromide administration reduced the mean duration of burying episodes in Fmr1 mutants and their wild-type controls. Furthermore, this treatment reduced the number of burying episodes, shakes and circling episodes to wild-type levels in knockout mice. (B) In the Y-maze, bromide treatment suppressed perseverative same arm returns in Shank3B1$^{-/-}$ mice. Data are presented as mean±sem. Comparison to vehicle-treated wild-type group: three stars: p<0.001 (two-way analysis of variance followed by Newman-Keules post-hoc test).

Measures of Anxiety

In the marble burying test, Shank3B knockout mice displayed a severe deficit in burying; bromide treatment reduced burying in both wild-type and mutant lines (genotype effect: $F_{1,28}$=198.7, p<0.0001; dose effect: $F_{1,28}$=4.8, p<0.05).

In the novelty-suppressed feeding test, Shank3B knockout mice took longer to eat of the food pellets and bromide administration normalized this feeding latency to wild-type level (genotype effect: $F_{1,28}=22.9$, $p<0.0001$; dose effect: $F_{1,28}=27.6$, $p<0.0001$; genotype×dose: $F_{1,28}=35.0$, $p<0.0001$). This treatment did not rescued diminished food intake of mutants when placed back in their home cage (genotype effect: $F_{1,28}=15.6$, $p<0.001$). Together, these data show that bromide can reduce exacerbated anxiety in mice lacking the Shank3B gene.

Figure 11:
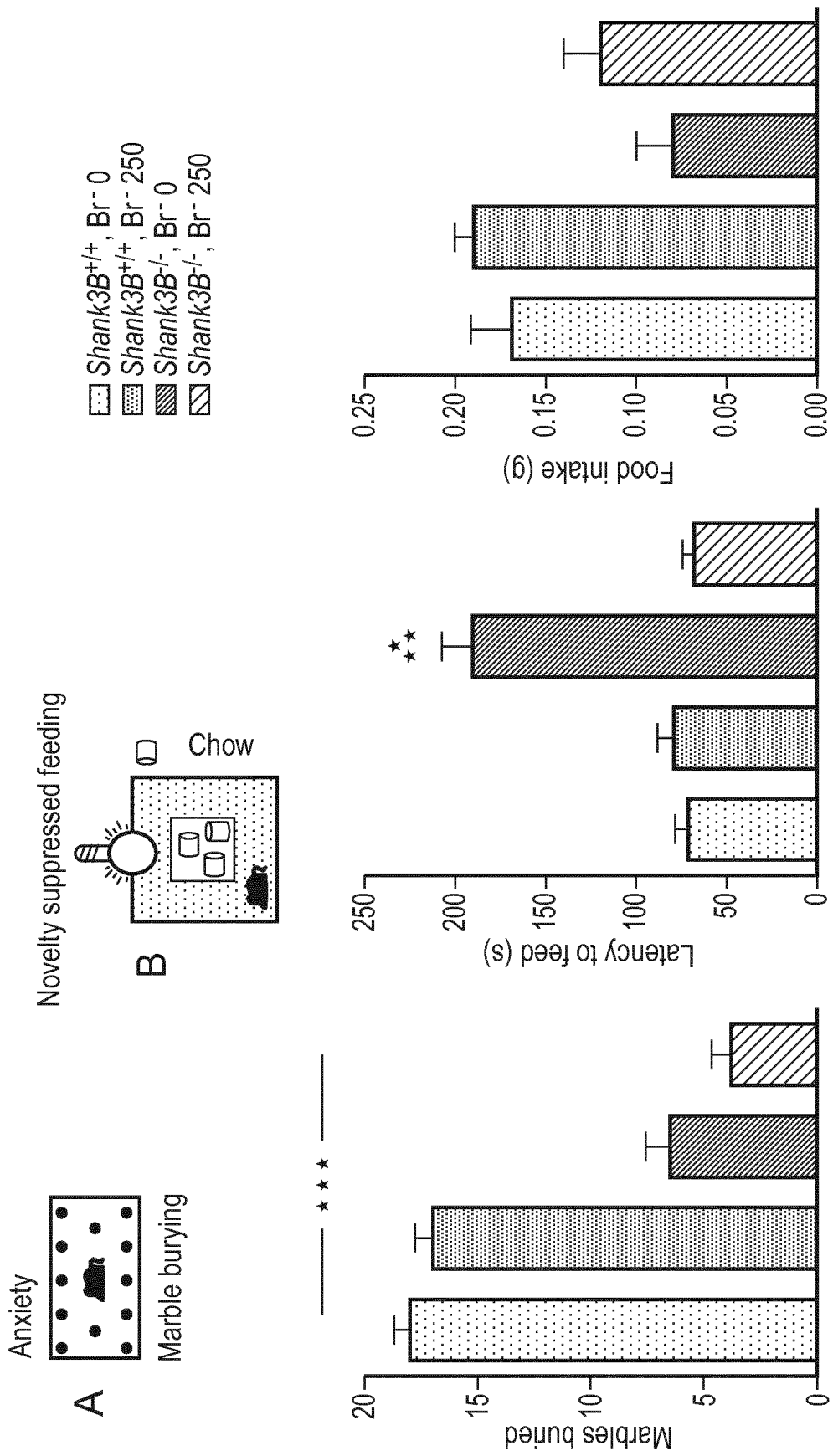
FIG. 11 shows the effect of chronic bromide administration on anxiety in Shank3B null mice.

FIG. 11 depicts the effects of chronic bromide treatment on measures of anxiety in Shank3B knockout mice. (A) In the marble burying test, mutant animals buried less marbles than wild-type controls, and bromide treatment had no significant effect. (B) In the novelty-suppressed feeding test, bromide administration normalized the latency to feed in Shank3B1$^{-/-}$ animals to wild-type level. Data are presented as mean±sem. Comparison to vehicle-treated wild-type group: one star: $p<0.05$ (two-way analysis of variance followed by Newman-Keules post-hoc test).

Conclusions

Behavioral experiments following repeated administration of sodium bromide at the doses of 125, 250 and 500 mg/kg in the mu opioid receptor knockout mouse model of autism unravel promising dose-dependent pharmacotherapeutic potential to relieve autistic syndrome. Indeed, after a week of daily bromide injection, Oprm1$^{-/-}$ mice displayed significant improvement of their social abilities as illustrated by increased direct social interaction and restored social preference in the three-chamber test as compared to vehicle-treated counterparts. This restoration of social interaction was associated with a significant decrease in motor and cognitive stereotypies, thus demonstrating beneficial effects of bromide administration on the second core symptom of autism. Finally, bromide administration relieved comorbid excessive anxiety in Oprm1$^{-/-}$ mice.

In this model, bromide demonstrated superior efficacy as compared to bumetanide in restoring social interaction and social preference parameters. In the social interaction test, bromide treatment produced bigger increases in the time spent in social contact, number of nose contacts, mean duration of these contacts, number of following episodes, number of paw contacts and their duration in mice lacking Oprm1 gene than bumetanide administration. The suppressive effects of both treatments on grooming episodes, including those occurring after a social contact, were comparable. In the three-chamber test, although bumetanide treatment, as bromide administration, successfully restored a preference for spending time in the compartment with the mouse (as shown in (Eftekhari et al, 2014; Holmes et al, 2015)) and increased the number of close contacts with this mouse, it failed to restore the duration of each of these contacts, leading to an absence of effect on the time spent in close contact with the mouse in Oprm1 mutants. This result shows that restoration of social preference by bromide in this test was qualitatively superior to this obtained with bumetanide. Limited effects of bumetanide may be related to its low ability to cross the blood brain barrier (Romermann et al, 2017), where bromide ions easily cross this barrier allowing them to reach high concentrations in the central nervous system. Together, these data indicate that bromide administration was a more efficient treatment than bumetanide in relieving social deficits in our mouse model, suggesting a highly promising therapeutic potential to restore social abilities in patients with ASD.

The observations of relieving effects of bromide administration were replicated for the dose of 250 mg/kg in two more genetic murine models of autism, Fmr1 and Shank3B knockout mice. Importantly, Oprm1, Fmr1 and Shank3B genes are unrelated, although they all code for synaptic proteins. Beneficial effects of bromide administration in three entirely different genetic murine models predicts high translational potential in patients with autism, despite high heterogeneity in etiology and symptoms.

REFERENCES

Abbeduto L, McDuffie A, Thurman A J (2014). The fragile X syndrome-autism comorbidity: what do we really know? *Front Genet* 5: 355.

Argyropoulos A, Gilby K L, Hill-Yardin E L (2013). Studying autism in rodent models: reconciling endophenotypes with comorbidities. *Front Hum Neurosci* 7: 417.

Bardoni B, Davidovic L, Bensaid M, Khandjian E W (2006). The fragile X syndrome: exploring its molecular basis and seeking a treatment. *Expert Rev Mol Med* 8(8): 1-16.

Becker J A, Clesse D, Spiegelhalter C, Schwab Y, Le Merrer J, Kieffer B L (2014). Autistic-like syndrome in mu opioid receptor null mice is relieved by facilitated mGluR4 activity. *Neuropsychopharmacology* 39(9): 2049-2060.

Budimirovic D B, Kaufmann W E (2011). What can we learn about autism from studying fragile X syndrome? *Dev Neurosci* 33(5): 379-394.

Cinque C, Pondiki S, Oddi D, Di Certo M G, Marinelli S, Troisi A, et al (2012). Modeling socially anhedonic syndromes: genetic and pharmacological manipulation of opioid neurotransmission in mice. *Transl Psychiatry* 2: e155.

Consortium TD-BFX (1994). Fmr1 knockout mice: a model to study fragile X mental retardation. *Cell* 78(1): 23-33.

Crawley J N (2007). Mouse behavioral assays relevant to the symptoms of autism. *Brain pathology* 17(4): 448-459.

D'Hooge R, Nagels G, Franck F, Bakker C E, Reyniers E, Storm K, et al (1997). Mildly impaired water maze performance in male Fmr1 knockout mice. *Neuroscience* 76(2): 367-376.

Deidda G, Parrini M, Naskar S, Bozarth I F, Contestabile A, Cancedda L (2015). Reversing excitatory GABAAR signaling restores synaptic plasticity and memory in a mouse model of Down syndrome. *Nat Med* 21(4): 318-326.

Durand C M, Betancur C, Boeckers T M, Bockmann J, Chaste P, Fauchereau F, et al (2007). Mutations in the gene encoding the synaptic scaffolding protein SHANK3 are associated with autism spectrum disorders. *Nat Genet* 39(1): 25-27.

Eftekhari S, Shahrokhi A, Tsintsadze V, Nardou R, Brouchoud C, Conesa M, et al (2014). Response to Comment on "Oxytocin-mediated GABA inhibition during delivery attenuates autism pathogenesis in rodent offspring". *Science* 346(6206): 176.

Garbugino L, Centofante E, D'Amato F R (2016). Early Social Enrichment Improves Social Motivation and Skills in a Monogenic Mouse Model of Autism, the Oprm1 (−/−) Mouse. *Neural Plast* 2016: 5346161.

Gaveriaux-Ruff C, Kieffer B L (2002). Opioid receptor genes inactivated in mice: the highlights. *Neuropeptides* 36(2-3): 62-71.

Gigliucci V, Leonzino M, Busnelli M, Luchetti A, Palladino V S, D'Amato F R, et al (2014). Region specific up-regulation of oxytocin receptors in the opioid Oprm1 (−/−) mouse model of autism. *Front Pediatr* 2: 91.

Harony-Nicolas H, De Rubeis S, Kolevzon A, Buxbaum J D (2015). Phelan McDermid Syndrome: From Genetic Discoveries to Animal Models and Treatment. *J Child Neurol* 30(14): 1861-1870.

Holmes G L, Tian C, Hernan A E, Flynn S, Camp D, Barry J (2015). Alterations in sociability and functional brain connectivity caused by early-life seizures are prevented by bumetanide. *Neurobiology of disease* 77: 204-219.

Jamot L, Matthes H W, Simonin F, Kieffer B L, Roder J C (2003). Differential involvement of the mu and kappa opioid receptors in spatial learning. *Genes Brain Behav* 2(2): 80-92.

Kidd S A, Lachiewicz A, Barbouth D, Blitz R K, Delahunty C, McBrien D, et al (2014). Fragile X syndrome: a review of associated medical problems. *Pediatrics* 134(5): 995-1005.

Lozano R, Hare E B, Hagerman R J (2014). Modulation of the GABAergic pathway for the treatment of fragile X syndrome. *Neuropsychiatr Dis Treat* 10: 1769-1779.

Maurin T, Zongaro S, Bardoni B (2014). Fragile X Syndrome: From molecular pathology to therapy. *Neurosci Biobehav Rev* 46P2: 242-255.

McNaughton C H, Moon J, Strawderman M S, Maclean K N, Evans J, Strupp B J (2008). Evidence for social anxiety and impaired social cognition in a mouse model of fragile X syndrome. *Behav Neurosci* 122(2): 293-300.

Moles A, Kieffer B L, D'Amato F R (2004). Deficit in attachment behavior in mice lacking the mu-opioid receptor gene. *Science* 304(5679): 1983-1986.

Monteiro P, Feng G (2017). SHANK proteins: roles at the synapse and in autism spectrum disorder. *Nat Rev Neurosci* 18(3): 147-157.

Oddi D, Crusio W E, D'Amato F R, Pietropaolo S (2013). Monogenic mouse models of social dysfunction: implications for autism. *Behav Brain Res* 251: 75-84.

Padmashri R, Reiner B C, Suresh A, Spartz E, Dunaevsky A (2013). Altered structural and functional synaptic plasticity with motor skill learning in a mouse model of fragile X syndrome. *J Neurosci* 33(50): 19715-19723.

Peca J, Feliciano C, Ting J T, Wang W, Wells M F, Venkatraman T N, et al (2011). Shank3 mutant mice display autistic-like behaviours and striatal dysfunction. *Nature* 472(7344): 437-442.

Pietropaolo S, Guilleminot A, Martin B, D'Amato F R, Crusio W E (2011). Genetic-background modulation of core and variable autistic-like symptoms in Fmr1 knock-out mice. *PLoS One* 6(2): e17073.

Romermann K, Fedrowitz M, Hampel P, Kaczmarek E, Toliner K, Erker T, et al (2017). Multiple blood-brain barrier transport mechanisms limit bumetanide accumulation, and therapeutic potential, in the mammalian brain. *Neuropharmacology* 117: 182-194.

Rotschafer S E, Trujillo M S, Dansie L E, Ethell I M, Razak K A (2012). Minocycline treatment reverses ultrasonic vocalization production deficit in a mouse model of Fragile X Syndrome. *Brain Res* 1439: 7-14.

Roy S, Liu H C, Loh H H (1998). mu-Opioid receptor-knockout mice: the role of mu-opioid receptor in gastrointestinal transit. *Brain research Molecular brain research* 56(1-2): 281-283.

Roy S, Watkins N, Heck D (2012). Comprehensive analysis of ultrasonic vocalizations in a mouse model of fragile X syndrome reveals limited, call type specific deficits. *PLoS One* 7(9): e44816.

Roy S, Zhao Y, Allensworth M, Farook M F, LeDoux M S, Reiter L T, et al (2011). Comprehensive motor testing in Fmr1-KO mice exposes temporal defects in oromotor coordination. *Behav Neurosci* 125(6): 962-969.

Silverman J L, Yang M, Lord C, Crawley J N (2010). Behavioural phenotyping assays for mouse models of autism. *Nat Rev Neurosci* 11(7): 490-502.

Spencer C M, Alekseyenko O, Hamilton S M, Thomas A M, Serysheva E, Yuva-Paylor L A, et al (2011). Modifying behavioral phenotypes in Fmr1KO mice: genetic background differences reveal autistic-like responses. *Autism Res* 4(1): 40-56.

Spencer C M, Alekseyenko O, Serysheva E, Yuva-Paylor L A, Paylor R (2005). Altered anxiety-related and social behaviors in the Fmr1 knockout mouse model of fragile X syndrome. *Genes Brain Behav* 4(7): 420-430.

Tabet R, Moutin E, Becker J A, Heintz D, Fouillen L, Flatter E, et al (2016). Fragile X Mental Retardation Protein (FMRP) controls diacylglycerol kinase activity in neurons. *Proc Natl Acad Sci USA* 113(26): E3619-3628.

Van Dam D, D'Hooge R, Hauben E, Reyniers E, Gantois I, Bakker C E, et al (2000). Spatial learning, contextual fear conditioning and conditioned emotional response in Fmr1 knockout mice. *Behav Brain Res* 117(1-2): 127-136.

Varghese M, Keshav N, Jacot-Descombes S, Warda T, Wicinski B, Dickstein D L, et al (2017). Autism spectrum disorder: neuropathology and animal models. *Acta neuropathologica*.

Wohr M, Moles A, Schwarting R K, D'Amato F R (2011). Lack of social exploratory activation in male mu-opioid receptor KO mice in response to playback of female ultrasonic vocalizations. *Soc Neurosci* 6(1): 76-87.

Yan Q J, Asafo-Adjei P K, Arnold H M, Brown R E, Bauchwitz R P (2004). A phenotypic and molecular characterization of the fmr1-tm1Cgr fragile X mouse. *Genes Brain Behav* 3(6): 337-359.

Example 2

Material and Methods

As discussed above, the subjects, materials and methods of Example 1 and 2 are identical.

Time Line of Drug Treatment and Behavioural Testing

Figure 12:
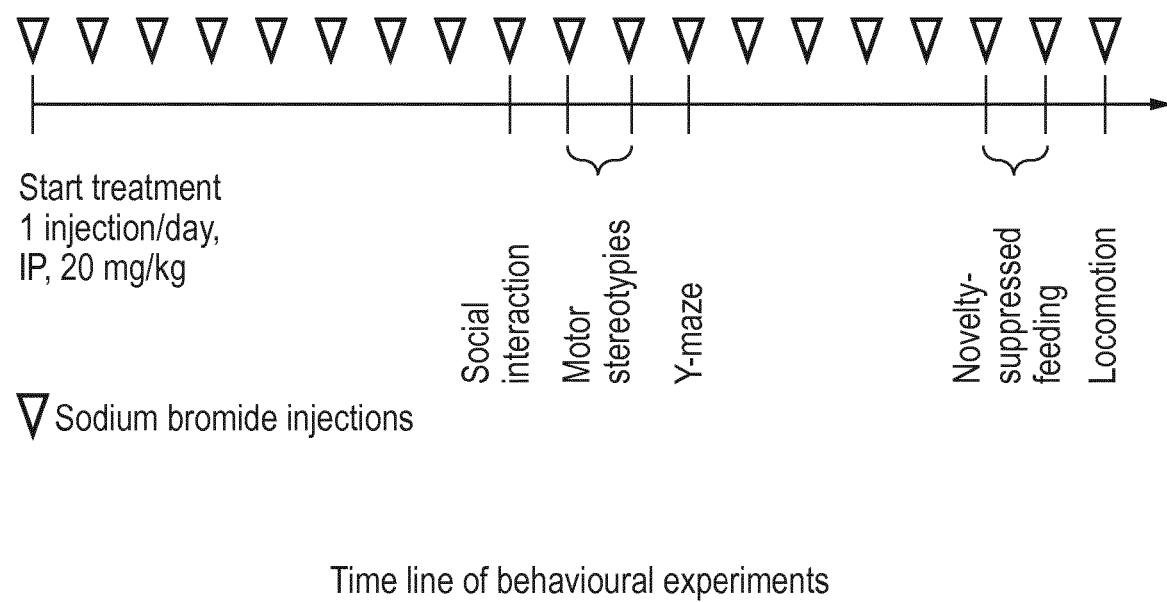
FIG. 12 shows the duration of chronic treatment and order of behavioural assays of Example 2.

Duration of chronic treatment and order of behavioural assays are displayed in FIG. 12. Testing order was chosen to limit the impact of stress on further behavioral assessments.

Statistical Analyses

Statistical analyses were performed as described above.

Results

Measures of Sociability

Deficient social interactions are the most remarkable core symptom of autism in humans. We assessed the effects of chronic bromide treatment on social abilities in $Oprm1^{+/+}$ mice and wild-type counterparts using the direct, dyadic, social interaction test.

In this test, chronic bromide administration demonstrated beneficial effects by increasing, in mutant animals, and more significantly in males than in females (bromide effects were detected since the dose of 250 mg/kg in male knockouts while it was observed only at the highest dose in females), the time spent in close contact (gender effect: $F_{1,35}=46.6$, $p<0.0001$; treatment effect: $F_{2,35}=43.1$, $p<0.0001$; genotype×treatment: $F_{2,35}=23.1$, $p<0.0001$; gender× treatment: $F_{2,35}=9.9$, $p<0.001$; genotype×gender×treatment: $F_{2,35}=11.2$, $p<0.001$), the number, time spent in and duration of nose and paw contacts (number of nose contacts: gender effect: $F_{1,35}=38.3$, $p<0.0001$; treatment effect: $F_{2,35}=19.7$, $p<0.0001$; genotype×gender: $F_{1,35}=5.2$, $p<0.05$; genotype×treatment: $F_{2,35}=18.6$, $p<0.0001$; gender×treatment: $F_{2,35}=13.9$, $p<0.001$; genotype×gender×treatment: $F_{2,35}=8.4$, $p<0.01$;

time spent in nose contact: gender effect: $F_{1,35}=44.2$, $p<0.0001$; treatment effect: $F_{2,35}=38.5$, $p<0.0001$;

genotype×treatment: $F_{2,35}=21.5$, $p<0.0001$; gender×treatment: $F_{2,35}=10.5$, $p<0.001$; genotype×gender×treatment: $F_{2,35}=10.5$, $p<0.001$;

nose contact duration: genotype effect: $F_{1,35}=15.5$, $p<0.001$; gender effect: $F_{1,35}=16.5$, $p<0.001$; treatment effect: $F_{2,35}=57.5$, $p<0.0001$; genotype×treatment: $F_{2,35}=35.6$, $p<0.0001$; gender×treatment: $F_{2,35}=10.4$, $p<0.001$; genotype×gender×treatment: $F_{2,35}=7.6$, $p<0.01$;

number of paw contacts: gender effect: $F_{1,35}=6.7$, $p<0.05$; treatment effect: $F_{2,35}=17.2$, $p<0.0001$; genotype×treatment: $F_{2,35}=7.5$, $p<0.01$; genotype×gender×treatment: $F_{2,35}=3.2$, $p<0.05$;

time spent in paw contact: gender effect: $F_{1,35}=11.0$, $p<0.01$; treatment effect: $F_{2,35}=20.6$, $p<0.0001$; genotype×treatment: $F_{2,35}=10.1$, $p<0.001$; genotype×gender×treatment: $F_{2,35}=4.7$, $p<0.05$;

paw contact duration: genotype: $F_{1,35}=7.5$, $p<0.01$; treatment effect: $F_{2,35}=33.8$, $p<0.0001$; genotype×treatment: $F_{2,35}=21.1$, $p<0.0001$; genotype×gender×treatment: $F_{2,35}=5.7$, $p<0.01$);

and the number of following episodes (gender effect: $F_{1,35}=15.9$, $p<0.001$; treatment effect: $F_{2,35}=21.4$, $p<0.0001$; genotype×treatment: $F_{2,35}=7.6$, $p<0.01$; gender×treatment: $F_{2,35}=6.6$, $p<0.01$; genotype×gender×treatment: $F_{2,35}=3.7$, $p<0.05$).

Bromide treatment also reduced the number of grooming episodes (genotype effect: $F_{1,35}=4.6$, $p<0.05$; treatment effect: $F_{2,35}=9.3$, $p<0.001$), time spent grooming (treatment effect: $F_{2,35}=12.0$, $p<0.001$; genotype×gender: $F_{2,35}=6.9$, $p<0.05$; gender×treatment: $F_{2,35}=3.7$, $p<0.05$), duration of grooming episodes (treatment effect: $F_{2,35}=3.9$, $p<0.05$; genotype×gender: $F_{2,35}=7.2$, $p<0.05$) and number of grooming episodes occurring immediately after a close contact (genotype effect: $F_{1,35}=19.6$, $p<0.0001$; treatment effect: $F_{2,35}=25.1$, $p<0.0001$; genotype×treatment: $F_{2,35}=23.0$, $p<0.0001$), in male and female Oprm1$^{-/-}$ animals (FIG. 13).

Therefore chronic bromide treatment was able to restore social interaction in mu opioid null mice.

Figure 13:
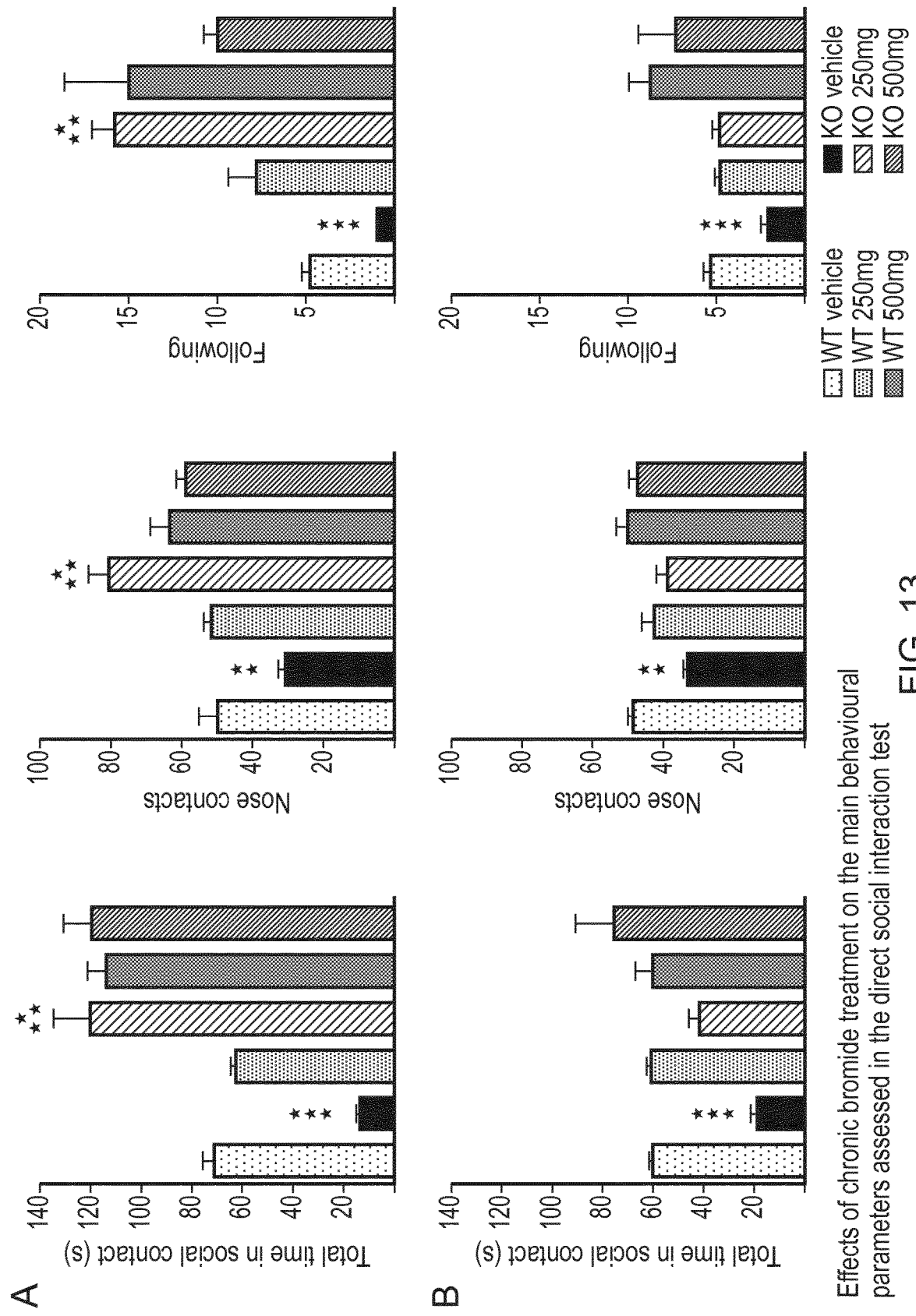
FIG. 13 shows the effects of chronic bromide treatment on the main behavioural parameters assessed in the direct social interaction test.

FIG. 13 shows the effects of chronic bromide treatment on the main behavioral parameters assessed in the direct social interaction test. (A) Chronic bromide administration increased the total amount of time spent in social contact in male wild-type (WT) and mu opioid receptor knockout (KO) mice, and increased the number of nose contacts and following episodes in mutants at both doses. (B) Chronic bromide administration increased the total amount of time spent in social contact, the number of nose contacts and following episodes in female mutant mice only, in a dose dependent manner. Data are presented as mean±sem. Genotype comparison: one star: $p<0.05$; two stars: $p<0.01$; three stars: $p<0.001$ (three-way analysis of variance followed by Newman-Keules post-hoc test).

Measures of Repetitive Behaviour

We assessed the effects of chronic bromide treatment on repetitive behavior in mu opioid receptor knockout mice by scoring the presence of spontaneous stereotypies and by evaluating the pattern of exploration in the Y-maze in these mutants and their wild-type counterparts.

Chronic bromide treatment increased the number of rearing episodes in wild-type and not knockout animals, in males since the dose of 250 mg/kg, and in females at the dose of 500 mg/kg only (gender effect: $F_{1,35}=6.4$, $p<0.05$; treatment effect: $F_{2,35}=15.2$, $p<0.0001$; genotype×gender: $F_{2,35}=4.7$, $p<0.05$; gender×treatment: $F_{2,35}=3.7$, $p<0.05$).

Bromide treatment similarly increased the number of grooming episodes and male and female wild-type mice, but not in mutants (genotype effect: $F_{1,35}=5.4$, $p<0.05$; genotype×treatment: $F_{2,35}=4.1$, $p<0.05$). Chronic bromide did not modify the number of burying episodes (treatment effect: $F_{2,35}=2.6$, NS; genotype×treatment: $F_{2,35<1}$, NS) and their duration (treatment effect: $F_{2,35}=2.1$, NS; genotype×treatment: $F_{2,35}=1.2$, NS) mice but decreased the time sent burying in all treated animals (treatment effect: $F_{2,35}=4.4$, $p<0.05$; genotype×treatment: $F_{2,35<1}$, NS).

Figure 14:
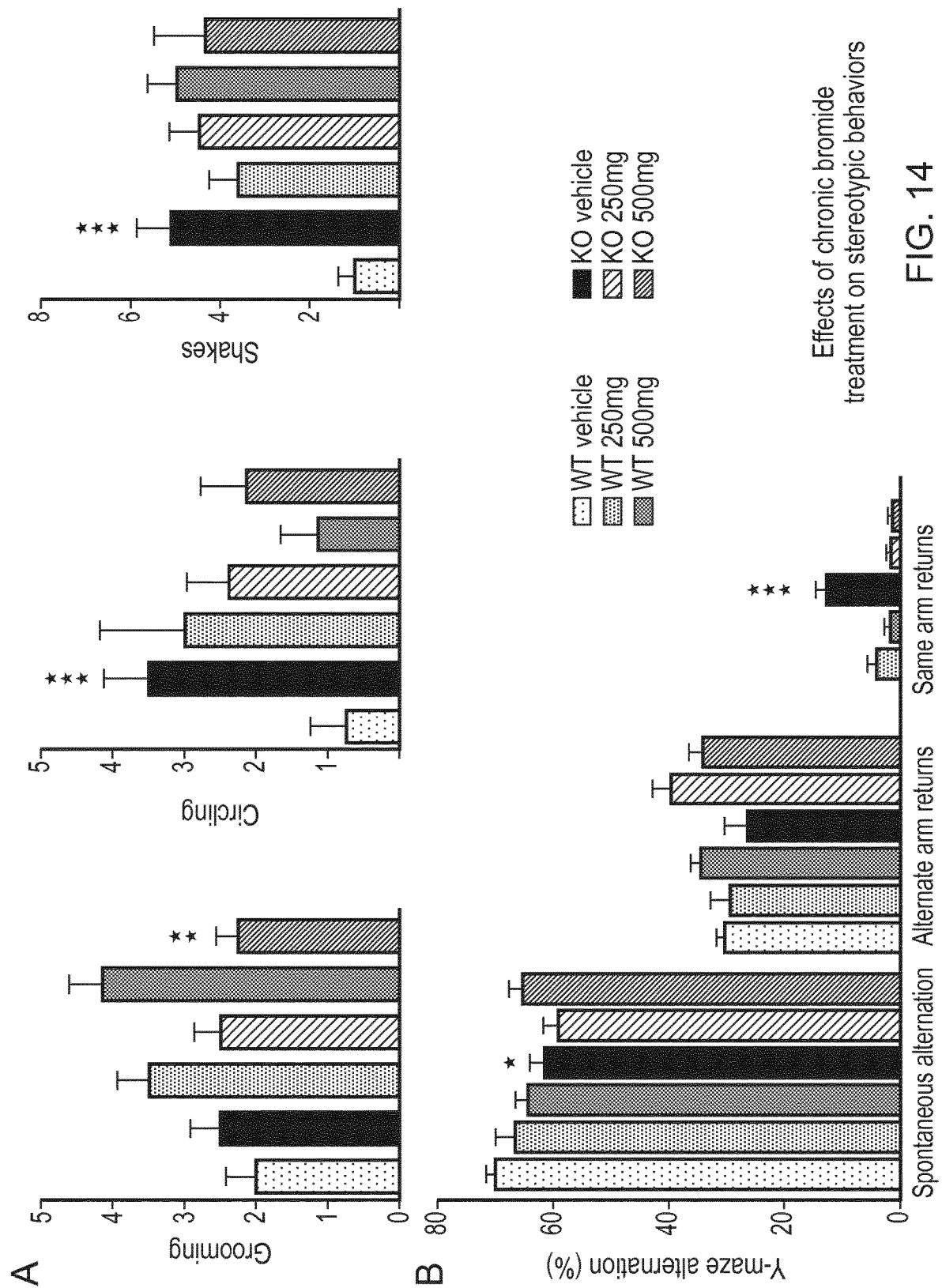
FIG. 14 shows the effects of chronic bromide treatment on stereotypic behaviours.

Bromide administration had no effect on circling behavior (genotype effect: $F_{1,35}=4.4$, $p<0.05$; genotype×treatment: $F_{2,35<1}$, NS) but increased the number of head shakes in male and female wild-type mice, not in mutants (genotype effect: $F_{1,35}=6.3$, $p<0.05$; genotype×treatment: $F_{2,35}=5.9$, $p<0.01$) (FIG. 14).

In the Y-maze exploration test, mutant animals showed a decrease in spontaneous alternation rates (Genotype effect: $F_{1,35}=7.6$, $p<0.001$), suggesting altered exploration patterns, with male mice performing better than females (Gender×treatment: $F_{2,35}=3.4$, $p<0.05$). This change was the reflect of an increased number of same arm returns in Oprm1$^{-/-}$ mice, demonstrating perseverative cognitive stereotypies in these animals (Genotype effect: $F_{1,35}=15.4$, $p<0.0001$).

Chronic bromide treatment normalized the ratio of same arm returns in knockout mice (treatment effect: $F_{2,35}=12.1$, $p<0.0001$; genotype×treatment: $F_{2,35}=32.5$, $p<0.0001$). Chronic bromide administration meanwhile increased the number of alternate arm returns, more significantly in mutants than in wild-type controls (Treatment effect: $F_{2,35}=3.6$, $p<0.05$; genotype×treatment: $F_{2,35}=4.1$, $p<0.05$) and more in females than in males (Gender effect: $F_{1,35}=5.5$, $p<0.05$; gender×treatment: $F_{2,35}=3.5$, $p<0.05$) (FIG. 14).

In conclusion, chronic bromide had little effect on motor stereotypies in mu opioid receptor knockout mice, but relieved cognitive stereotypies (perseveration).

FIG. 14 shows the effects of chronic bromide treatment on stereotypic behaviors. (A) Chronic bromide administration increased grooming episodes in wild-type (WT) animals without effects in mu opioid receptor knockouts (KO), had little effect on the number of circling episodes and increased the number of head shakes in control mice to the level of mutants. (B) In contrast, bromide treatment restored spontaneous alternation in mu opioid receptor null mice. Indeed, despite a tendency to increase alternate arm returns, bromide abolished same arm returns in mutants when exploring the Y-maze, demonstrating efficiency in reducing cognitive stereotypies. Data are presented as mean±sem. Genotype comparison: one star: $p<0.05$; two stars: $p<0.01$; three stars: $p<0.001$ (three-way analysis of variance followed by Newman-Keules post-hoc test).

Measure of Anxiety

We evaluated the effects of chronic bromide administration on anxiety levels using the novelty-suppressed feeding test. Bromide treatment decreased in wild-type, and normalized in mu opioid receptor null mice, the latency to feed (Genotype effect: $F_{1,35}=23.6$, $p<0.0001$, gender effect: $F_{2,35}=4.7$, $p<0.05$; treatment effect: $F_{2,35}=21.1$, $p<0.0001$), indicating anxiolytic effects, and the dose of 250 mg/kg was more effective in males than in females (Gender×treatment: $F_{2,35}=10.1$, $p<0.001$). When returned to their home cage, female wild-type animals treated with bromide at 250 mg ate more than saline-treated animals, while bromide treatment increased food intake in mutants ($F_{1,35}=5.0$, $p<0.05$; gender effect: $F_{1,35}=7.5$, $p<0.01$; treatment effect: $F_{2,35}=3.6$, p<0.05; gender×treatment $F_{1,35}$=4.1, p<0.05), another sign of decreased anxiety (FIG. 15).

Figure 15:
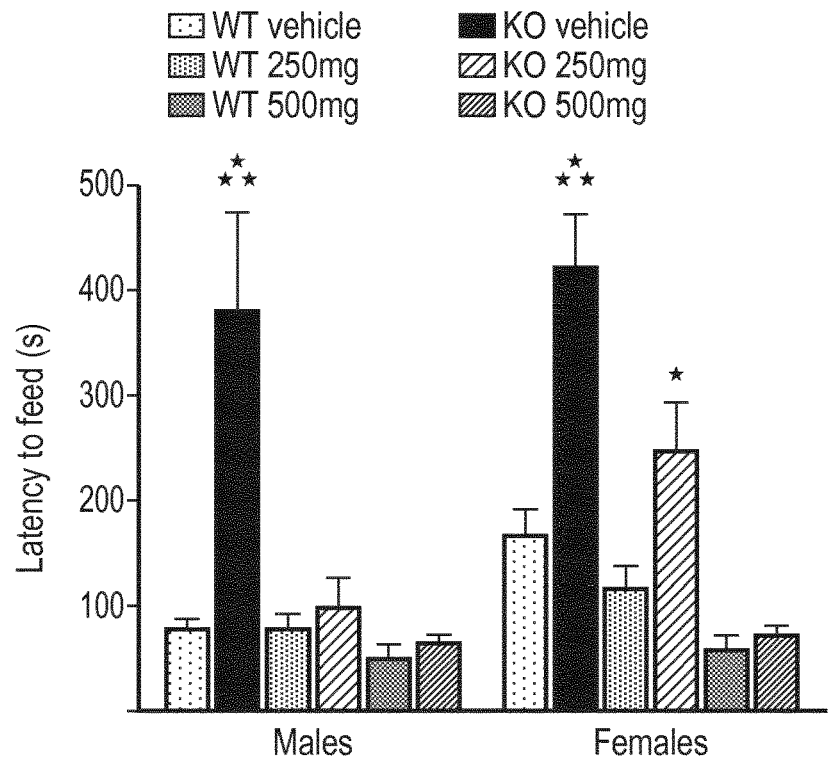
FIG. 15 shows the effects of chronic bromide treatment on the latency to feed in the novelty-suppressed feeding test.

FIG. 15 shows the effects of chronic bromide treatment on the latency to feed in the novelty-suppressed feeding test. Chronic bromide administration drastically reduced the latency to feed in the mu opioid receptor null mice, demonstrating anxiolytic action, with the maximal effect reached at the dose of 250 mg/kg in males and 500 mg/kg in females. Data are presented as mean±sem. Genotype comparison: one star: p<0.05; three stars: p<0.001 (three-way analysis of variance followed by Newman-Keules post-hoc test).

Measures of Activity

We assessed activity in bromide treated animals and controls in the course of the social interaction and Y-maze exploration test, as well as in a dedicated assay, videotracking of forward locomotion immediately before and after bromide injection.

In the direct social interaction test, chronic bromide at 250 mg/kg increased the number of rearing episodes in mu opioid receptor null mice, more significantly in males than in females (genotype effect: $F_{1,35}$=41.7, p<0.0001; treatment effect: $F_{2,35}$=7.7, p<0.01; genotype×gender: $F_{2,35}$=8.3, p<0.01; genotype×treatment: $F_{2,35}$=35.6, p<0.0001; gender×treatment: $F_{2,35}$=10.4).

In the Y-maze, chronic bromide administration at the dose of 250 mg/kg increased the number of arm entries in both genotypes and genders (treatment effect: $F_{2,35}$=7.5, p<0.01), an index of general locomotor activity.

Finally, we measured locomotor activity under bromide treatment using videotracking. During the course of the habituation run, locomotor activity was already higher in bromide treated animals (Time course effect: $F_{5,175}$=4.2, p<0.01; time course×treatment: $F_{10,175}$=1.9, p<0.05), in males since the dose of 250 mg/kg, and only at the dose of 500 mg/kg in females (time course×gender×treatment: $F_{10,175}$=2.26, p<0.05), indicating that bromide administration increased basal locomotor activity in mice. After bromide administration, locomotor activity was increased in mutant animals at the dose of 250 mg/kg, but not at 500 mg/kg, whereas this activity was not modified in controls at 250 mg/kg and was increased at 500 mg/kg (Genotype×treatment: $F_{2,35}$=6.0, p<0.01) (FIG. 16).

Altogether, these data suggest that chronic bromide treatment at the lower tested dose (250 mg/kg) increases locomotor activity in mice, with males being more sensitive to this effect.

Figure 16:
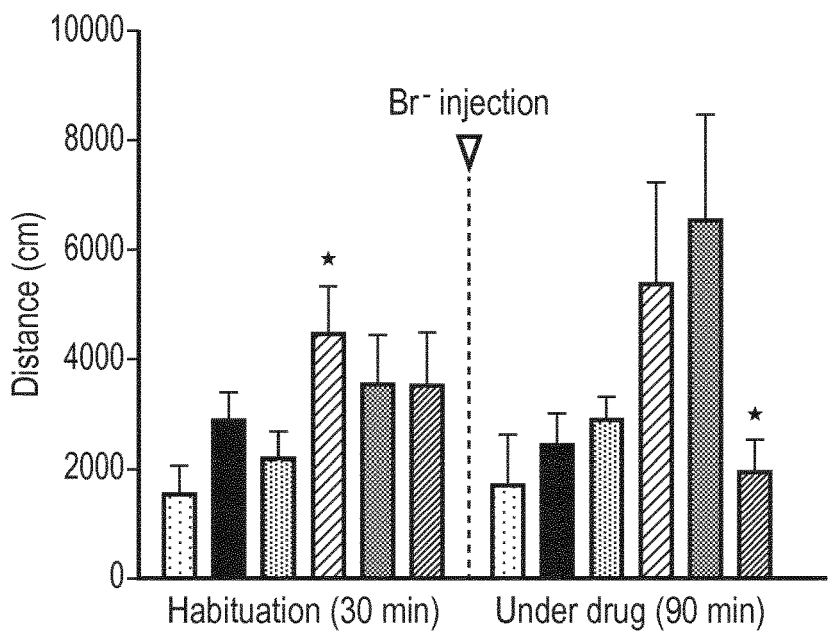
FIG. 16 shows the effects of chronic bromide treatment on locomotor activity measured by videotracking.

FIG. 16 shows the effects of chronic bromide treatment on locomotor activity measured by videotracking. During habituation and following bromide administration, mutant animals (KO) chronically treated with bromide displayed increased activity for the dose of 250 mg/kg. Such increase was observed in wild-type animals (WT) at the dose of 500 mg/kg only. Data are presented as mean±sem. Genotype comparison: one star: p<0.05 (four-way analysis of variance followed by Newman-Keules post-hoc test).

The invention claimed is:

1. A method of treating autism spectral disorder (ASD) caused by a mutation to mu opioid receptor (Oprm1) in a subject in need thereof, comprising
    selecting a subject with ASD caused by a mutation in Oprm1, and
    administering to the subject at least one source of bromide, wherein the source of bromide is selected from the group consisting of potassium bromide, sodium bromide, ammonium bromide, calcium bromide, calcium bromolactobionate, calcium galactogluconate bromide, calcium bromide lactobionate hexahydrate, calcium bromo-galactogluconate, calcium bromolactobionate, clidinium bromide, ferrous bromide, gold tribromide, hydrogen bromide, iron bromide, lithium bromide, magnesium bromide, radium bromide, strontium bromide, acecarbromal, bromazepam, bromazine, bromisoval, bromoforme, bromperidol, carbromal magnesium aspartate hydrobromide, galantamine bromohydrate, theobromine and mixtures thereof;
    wherein the administering step is sufficient to improve cognitive flexibility and relieves one or more additional symptoms of social deficit and/or exacerbated anxiety associated with ASD.

2. The method according to claim 1 wherein the one or more symptoms associated with ASD is selected from the group consisting of reduced social interaction, absence of interest in others, preference to remain alone, repetitive behaviours, unusual interests or behaviours, absence of understanding of personal space boundaries, avoidance or resistance to physical contact, repetitive motions, routine behaviours, impulsivity, and delays in social and learning skills.

3. The method according to claim 1, wherein the source of bromide is selected from the group consisting of potassium bromide, sodium bromide, ammonium bromide, calcium bromide, lithium bromide and mixtures thereof.

4. The method according to claim 3 wherein the source of bromide is sodium bromide or potassium bromide alone or in combination with one or more other sources of bromide.

5. The method according to claim 1, wherein administration of the source of bromide relieves social deficit.

6. The method according to claim 1, wherein administration of the source of bromide relieves exacerbated anxiety associated with ASD.

7. The method according to claim 1, wherein the subject is a male patient.

8. The method according to claim 1, wherein the source of bromide is administered in combination with a second pharmaceutically active compound selected from the group consisting of risperidone, aripiprazole, olanzapine, oxytocin, bumetanide and caffeine.

9. The method according to claim 8, wherein the second pharmaceutically active compound is effective in relieving a symptom associated with ASD.

10. The method according to claim 8, wherein the second pharmaceutically active compound is selected from the group consisting of risperidone, aripiprazole, olanzapine, oxytocin and bumetanide.

11. The method according to claim 10, wherein the second pharmaceutically active compound is oxytocin or bumetanide.

12. The method according to claim 8, wherein the second pharmaceutically active compound is effective against bromide-related side effects.

13. The method according to claim 8, wherein the second pharmaceutically active compound is caffeine.

14. A method of treating autism spectral disorder (ASD) caused by a mutation to mu opioid receptor (Oprm1) in a subject in need thereof, comprising
    selecting a subject with ASD caused by a mutation in Oprm1;
    co-administering to the subject a source of bromide selected from the group consisting of potassium bromide, sodium bromide, ammonium bromide, calcium bromide, calcium bromolactobionate, calcium galactogluconate bromide, calcium bromide lactobionate hexahydrate, calcium bromo-galactogluconate, calcium bromolactobionate, clidinium bromide, ferrous bromide, gold tribromide, hydrogen bromide, iron bromide, lithium bromide, magnesium bromide, radium bromide, strontium bromide, acecarbromal, bromazepam, bromazine, bromisoval, bromoforme, bromperidol, carbromal magnesium aspartate hydrobromide, galantamine bromohydrate, theobromine and mixtures thereof; and a second pharmaceutically active agent selected from the group consisting of risperidone, aripiprazole, olanzapine, oxytocin, bumetanide and caffeine;

wherein the co-administering step is sufficient to improve cognitive flexibility and relieves one or more additional symptoms of social deficit and/or exacerbated anxiety associated with ASD.

15. The method according to claim 14, wherein the one or more additional symptoms of social deficit and/or exacerbated anxiety associated with ASD is selected from the group consisting of reduced social interaction, absence of interest in others, preference to remain alone, repetitive behaviours, unusual interests or behaviours, absence of understanding of personal space boundaries, avoidance or resistance to physical contact, repetitive motions, routine behaviours, impulsivity, and delays in social and learning skills.

* * * * *